(12) United States Patent
Sahin

(10) Patent No.: US 12,053,616 B2
(45) Date of Patent: Aug. 6, 2024

(54) FLUID RESPONSIVE DEVICES AND METHODS

(71) Applicant: The Trustees of Columbia University in the City of New York, New York, NY (US)

(72) Inventor: Ozgur Sahin, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 877 days.

(21) Appl. No.: 17/075,388

(22) Filed: Oct. 20, 2020

(65) Prior Publication Data

US 2021/0030958 A1  Feb. 4, 2021

Related U.S. Application Data

(63) Continuation of application No. PCT/US2019/028675, filed on Apr. 23, 2019.

(60) Provisional application No. 62/661,440, filed on Apr. 23, 2018.

(51) Int. Cl.
 *A61M 5/20* (2006.01)
 *A61K 35/00* (2006.01)
 *A61K 35/742* (2015.01)
 *A61K 47/38* (2006.01)
 (Continued)

(52) U.S. Cl.
 CPC ............ *A61M 5/20* (2013.01); *A61K 35/742* (2013.01); *A61K 47/38* (2013.01); *B25J 9/1095* (2013.01); *F15B 15/00* (2013.01); *A61K 2035/115* (2013.01)

(58) Field of Classification Search
 CPC .......... A61M 5/20; A61M 2005/14513; A61M 5/14593; A61M 31/002; A61M 5/168; A61M 5/14276; A61K 35/742; A61K 47/38; A61K 2035/115; B25J 9/1095; F15B 15/00
 See application file for complete search history.

(56) References Cited

U.S. PATENT DOCUMENTS

| | | |
|---|---|---|
| 5,935,593 A | 8/1999 | Ron et al. |
| 8,529,551 B2 | 9/2013 | Hood et al. |
| 9,067,047 B2 | 6/2015 | Wood, Jr. et al. |

(Continued)

FOREIGN PATENT DOCUMENTS

| | | | | |
|---|---|---|---|---|
| WO | WO-0100787 A2 * | 1/2001 | ............ | C07K 14/47 |
| WO | 2018089924 A2 | 5/2018 | | |

OTHER PUBLICATIONS

Chen et al., "Bacillus spores as building blocks for stimuli-responsive materials and nanogenerators," Nature Nanotechnology, Feb. 2014, vol. 9, pp. 137-141.

(Continued)

*Primary Examiner* — Theodore J Stigell
*Assistant Examiner* — Rachel T. Smith
(74) *Attorney, Agent, or Firm* — Potomac Law Group, PLLC

(57) ABSTRACT

Aspects provide fluid responsive actuators and methods of using fluid responsive actuators capable of generating a power-to-volume ratio sufficient to inject a drug from a syringe within an injection period from about 1 to about 60 seconds after exposure of the fluid responsive elements to a fluid. The fluid responsive actuators can be used to inject viscous drugs to a patient.

10 Claims, 20 Drawing Sheets

(51) Int. Cl.
*B25J 9/10* (2006.01)
*F15B 15/00* (2006.01)

(56) References Cited

U.S. PATENT DOCUMENTS

| | | |
|---|---|---|
| 2005/0066961 A1 | 3/2005 | Rand |
| 2005/0273054 A1 | 12/2005 | Asch |
| 2007/0135800 A1 | 6/2007 | Hood et al. |
| 2008/0269725 A1 | 10/2008 | Deem et al. |
| 2011/0172645 A1* | 7/2011 | Moga ............... A61M 37/0015 604/890.1 |
| 2011/0196232 A1 | 8/2011 | Kim et al. |
| 2013/0237808 A1 | 9/2013 | Wagner et al. |
| 2017/0067452 A1* | 3/2017 | Sahin ..................... H01G 5/16 |
| 2018/0028761 A1 | 2/2018 | Anand et al. |

OTHER PUBLICATIONS

Chen et al., "Scaling up nanoscale water-driven energy conversion into evaporation-driven engines and generators," Nature Communications, 2015, vol. 6, pp. 1-7, Macmillian Publishers Limited, New York, New York.

International Preliminary Report on Patentability dated Nov. 5, 2020, issued in International Application No. PCT/US2019/028675.

International Search Report and Written Opinion for International Application No. PCT/US2019/028675 dated Aug. 19, 2019.

Sahin et al., "Physical basis for the adaptive flexibility of Bacillus spore coats," Journal of The Royal Society, 2012, vol. 9, pp. 3156-3160, London, United Kingdom.

Unknown, "Electrical generator uses bacterial spores to harness power of evaporating water," ScienceDaily, 2014, 3 pages, Wyss Institute for Biologically Inspired Engineering at Harvard, Boston, Massachusetts.

Unknown, "How evaporation is used to power tiny engines," alive2green, 2015, 4 pages, https://alive2green.com/tag/bacillus-subtilis/.

* cited by examiner

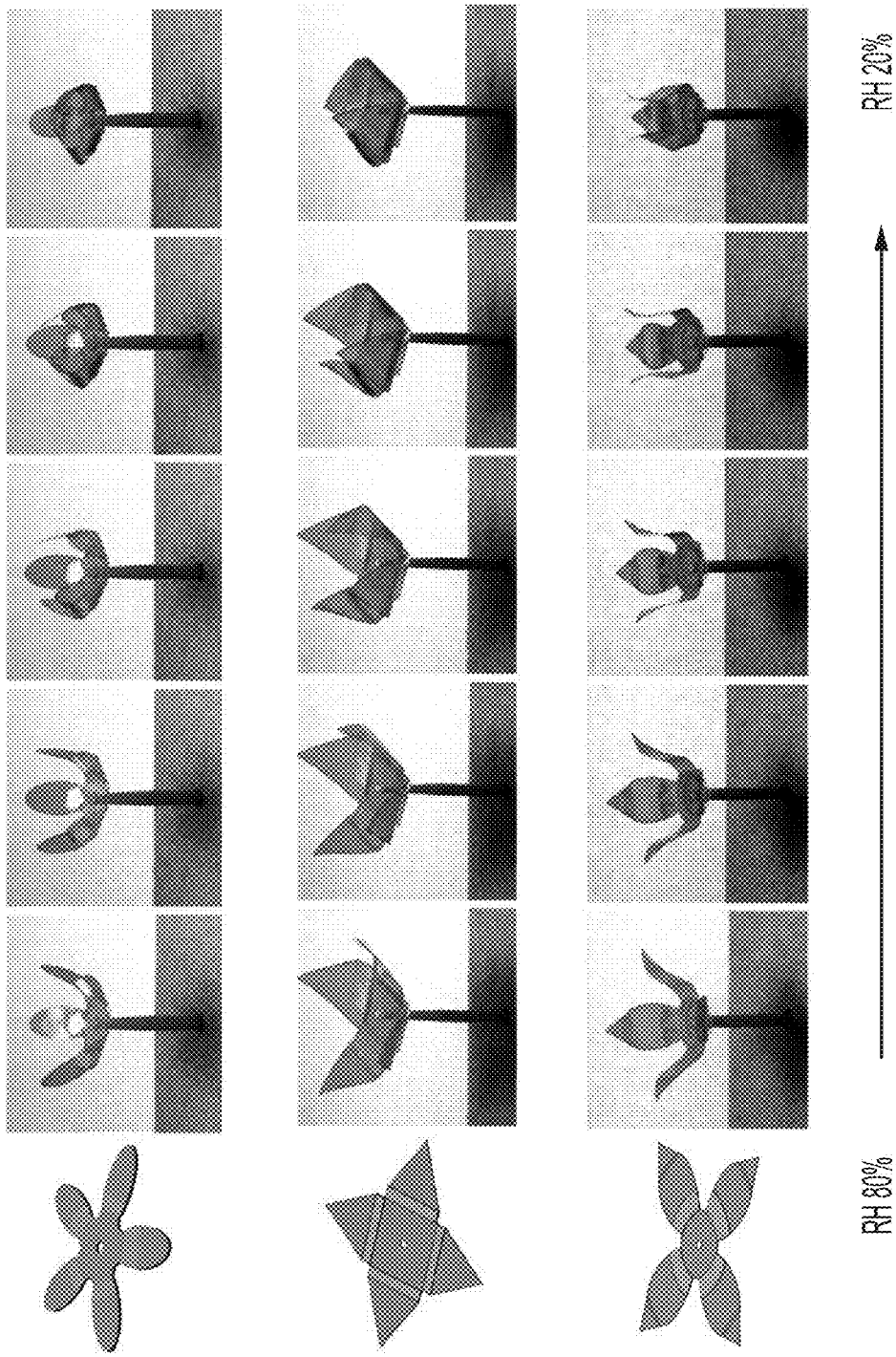

FLUID RESPONSIVE DEVICES AND METHODS

CROSS-REFERENCE TO RELATED APPLICATIONS

This application is a continuation of International Application No. PCT/US2019/028675 filed Apr. 23, 2019, which claims priority to, and the benefit of U.S. Provisional Patent Application No. 62/661,440 filed Apr. 23, 2018, both of which are hereby incorporated by reference in their entireties.

All references cited herein, including but not limited to patents and patent applications, are incorporated by reference in their entirety.

BACKGROUND

Soft actuators promise enhanced effectiveness of technologies that improve quality of human life including robotics, artificial muscles, energy harvesting, adaptive architecture, and adaptive textiles. The potency of these systems is presently limited by the performance and the practicality of their requisite actuators.

Fluid responsive materials are emerging as versatile alternatives to existing technologies that typically require invasive external stimuli such as high electric fields, or high temperatures and pressures. The term "fluid responsive materials" includes materials that can be activated by perturbations to the ambient humidity or with direct contact or perfusion of fluids such as water or alcohol. Such materials may be produced by natural or intentional fluctuations in environmental stimuli. In one aspect, various types of materials (e.g., graphene oxide, polymers, liquid crystals, paper and biologically-based materials) can serve as hygroscopic actuators, with curling and folding, walking, gripping, and power generation functions.

Fluid responsive materials can comprise "fluid responsive elements" (e.g., individual spores) that are each activated by perturbations to the ambient humidity or with natural or intentional fluctuations in environmental stimuli. The swelling, curling, folding, walking, gripping, and power generation functions of each humidity response element can be aggregated with other humidity response elements to generate a higher power density and other properties than an individual humidity response element.

Despite the potential of fluid responsive materials, relatively low work densities and slow response time for these materials limit the scope of applications. Studies of hygroscopic properties of *Bacillus* spores have shown that these dormant microorganisms exhibit actuation capabilities, with energy densities up to about 20 MJ m$^{-3}$. However, harnessing the actuation properties of spores as building blocks of macroscopic actuators has not been suggested. In addition, spores do not adhere strongly to each other, and therefore aggregating the energy densities of individual spores into macroscopic actuation energy is challenging.

SUMMARY

Aspects described herein provide fluid responsive actuators and methods of using the same. The fluid responsive actuators can aggregate the energy densities of individual spores after exposure to a fluid to generate actuation energy that can be used for a variety of applications that require generating actuation energy in a short period of time.

Fluid-responsive actuators described herein can be used in an injector (e.g., for injecting drugs into a patient) and can be advantageous compared to conventional injectors due to the gradual increase in pressure provided by fluid-responsive actuators. Spring loaded actuators, upon trigger, provide a sudden burst of force and pressure, which is slowly reduced as the plunger is pushed. This burst of pressure can damage the drug container, and create a loud sound that can cause anxiety in some patients and affect adherence to the treatment. The gradual increase in pressure with fluid-responsive actuation reduces the risk of damage to the drug container and the sound associated with actuation.

The fluid responsive actuators can comprise a plurality of fluid responsive elements capable of generating a power-to-volume ratio of at least about 10 kW $m^{-3}$ in response to exposure to a fluid (e.g., water), the fluid responsive elements having a tensile modulus greater than a maximum pressure generated by the fluid responsive elements when fluid is absorbed by the fluid responsive elements.

Further aspects provide fluid responsive injectors and methods of using the same. In this aspect, the fluid responsive injectors have a fluid chamber, a fluid responsive actuator, and a release mechanism for controlling contact between a fluid in the fluid chamber and the fluid response actuator, a drug chamber, and a needle. After the release mechanism permits contact between the fluid from the fluid chamber and the fluid responsive actuator, the fluid responsive actuator expands and creates a force sufficient to push a drug in the drug chamber through the needle within a predetermined activation period. The fluid responsive injectors can generate enough energy to permit injection of viscous drugs and fluids in a relatively short period of time compared to conventional fluid injectors.

BRIEF DESCRIPTION OF DRAWINGS

FIG. 1A shows an exemplary process of fabricating a fluid responsive actuator with a spore/adhesive mixture being applied to polyimide substrate;

FIG. 1B shows an exemplary process of curing the spore/adhesive mixture applied to the polyimide substrate with ultraviolet (UV) light;

FIG. 1C illustrates the expansion and contraction of a spore depending on the relative humidity (RH);

FIG. 1D illustrates the change in shape of an exemplary fluid responsive actuator depending on the presence of water (humid) and absence of water (dry);

FIG. 1E shows an exemplary fluid responsive actuator in 90% RH (relative humidity);

FIG. 1F shows an exemplary fluid responsive actuator in 20% RH;

FIG. 1G shows a side view scanning electron microscope (SEM) image of an exemplary fluid responsive actuator having a spore/adhesive layer (top) and substrate layer (bottom);

FIGS. 1H and 1I provide SEM images of an exemplary spore/adhesive mixture at two different magnifications;

FIGS. 2A-2B provide images of the change in curvature of exemplary spore/adhesive devices on polyimide substrate (actuator devices) when the relative humidity was alternated between 90% RH (FIG. 2A) and 10% RH (FIG. 2B) at 23° C.;

FIG. 2C provides the radius of curvature from the images of FIGS. 2A-2B;

FIG. 2D provides work density (x-axis) and power density (y-axis) of exemplary actuator devices with NOA (Norland Optical Adhesive) 81 and NEA (Norland Electronic Adhesive) 121 adhesives and spore/adhesive mixing ratios of 25%, 40%, and 50%;

FIG. 2E provides time constants at different mixing ratios (25%, 40%, and 50%) for NOA 81 and NEA 121 adhesives in exemplary actuator devices;

FIGS. 4A-4C illustrates the unfolding of three exemplary actuator devices as the relative humidity is reduced from 80% to 20%;

FIG. 5 shows an exemplary time course of rapid unfolding of actuator devices (spore coated tape) dipped in water, lifted, and permitted to air dry;

FIGS. 6A-6B illustrate an exemplary fluid activated injector devices in accordance with aspects described herein;

FIGS. 7A-7B illustrate the exemplary fluid activated injector devices shown in FIGS. 6A-6B with the addition of an optional bladder to generate or store water for the water chamber;

FIG. 7C illustrates an aspect of the actuator devices of FIGS. 6A-7B having a passage in the center of a stop that withstands the force of the expanding actuator;

FIG. 7D illustrates an aspect of the actuator devices of FIGS. 6A-7C having a water injector to control introduction of fluid to the actuator device;

FIGS. 8A-8B illustrate an exemplary actuator device having fluid responsive stacked layers with holes, a spore/adhesion suspension disposed thereon, and channels for distributing water through the holes in the stacked layers;

FIGS. 9A-9F provide photographs of the actuator device illustrated in FIGS. 8A-8B having stacked layers without the holes and channels;

FIGS. 10A-10C illustrate an actuator device that can be formed with ramifying longitudinal channels formed by a mold used with a substrate;

FIGS. 10D-E shows a view of the ramifying channel network shown in FIGS. 10A-10C blackened against a layer of spores and adhesive (FIG. 10D) and with additional detail regarding the channel network (FIG. 10E);

FIG. 10F shows multiple stacked layers with a ramifying channel network, holes, and channels formed in the holes;

FIGS. 11A-11D illustrate an exemplary actuator device having stacks of spore/adhesive layers and fractal channels arranged in a closed loop (FIG. 11C) and in an open loop (FIG. 11D);

FIG. 12 illustrates an actuator device formed employing cellophane folded to form transverse and through-channels for distributing fluid to the actuator device;

FIG. 13 illustrates an aspect of an actuator using an adhesive material to provide lateral confinement for fluid-philic material (e.g., spores); and FIG. 14 shows an exemplary actuator device using a wicking material to promote the wetting of fluid-philic material in addition to, or instead of, using convective perfusion.

DETAILED DESCRIPTION

Presently disclosed are exemplary methods and devices for assembling fluid responsive materials and other materials as described herein into larger materials, while retaining and using their actuation properties. Aspects of the disclosed methods and devices strengthen spore-spore interactions in order to harness the energy densities of individual spores. Further aspects provide fluid response-based actuators comprising fluid responsive materials and optional adhesives (e.g., water soluble adhesives). In these aspects, for example, mixtures of spores and water-soluble adhesives can be deposited onto plastic films to create various actuators and energy harvesting devices. In these aspects, the collective work density of individual spores can be aggregated to perform energy intensive tasks. It is to be understood that other means including mechanical means can be used to harness the energy densities of individual spores.

In one aspect, spores can be aggregated to produce a spore-based fluid responsive actuator or deposited directly on to a substrate. Substrates can include any suitable material that can provide a support for the spores (e.g., polyimide).

In other aspects, spore-based actuators comprise adhesives (e.g., water compatible adhesives (e.g., polyvinyl alcohol), water-resistant adhesives) capable of achieving work densities of up to about 0.72 MJ $m^{-3}$, which is an order of magnitude higher than synthetic fluid responsive polymers. In addition to improving the work density of spore-based actuators, exemplary water-resistant adhesives facilitate additional capabilities. The UV-curability of these adhesives can be used in a 'spore lithography' technique that facilitates rapid fabrication of complex dynamic and/or adaptive structures. The water resistance of the spore-based actuators allows direct water-driven actuation, which reduces the response time of the actuator by nearly 100-fold. In this aspect, the water-driven actuation of these exemplary materials (e.g., spores and adhesives) offer specific power (power-to-mass ratio) values up to about 8.22 kW/kg, which is approximately two orders of magnitude higher than mammalian skeletal muscle. In one aspect, the water-driven actuators have specific power values between about 50 and about 284 W/kg. Corresponding power densities (power-to-volume ratios) can be determined, for example, by multiplying the specific power values with the mass density of the materials.

*Bacillus subtilis* spores exhibit hygroscopic actuation capabilities and have shown high energy densities which make them useful for actuator applications. However, creating tough macroscopic materials from spores pose challenges. For example, in order to transmit the high mechanical force from one spore to another, and between layers of spores, spores can be made to adhere to one another with, for example, a stiff and ductile filling material. Otherwise, individual spores can slip across each other during expansion and contraction, or cracks may occur within the actuator due to stress. In another aspect, the filling material can optionally not degrade in aqueous environments in order to take advantage of direct fluid-driven actuation.

Commercially available optical and electronical adhesives have been used in applications which have tight requirements for low moisture sensitivity. For example, adhesives can be hydrophobic and resistant to moisture. In another aspect, the adhesives can be Norland NOA 81 and NEA 121 (Norland Products, Inc.) since they provide satisfactory mechanical properties and are water resistant. Monomers of Norland NOA 81 and NEA 121 polymerize under UV light to create a tough hydrophobic adhesive. However, because Norland NOA 81 and NEA 121 are not soluble in water they can be dissolved in an organic solvent such as acetone. In one aspect, the spores can be suspended in this solution.

Spores are a resilient biomaterial and can withstand treatment with solvents such as acetone. This suspension (spores and Norland NOA 81 or NEA 121 in acetone) can be deposited on substrate surfaces and rapidly cured with low power UV light (FIG. 1A, 1B). The fast curing of the adhesive and the high evaporation rate of the acetone both contributes to rapid fabrication. This is much faster than the methods using water soluble adhesives used previously, hampered by slow evaporation of water. Alternate materials with similar properties can be used in place of Norland NOA 81 or NEA 121 and acetone to achieve the properties described herein. In addition, water-soluble adhesives can be used is aspects described herein.

The work and power generated by the actuator can be measured, for example, using polyimide tape as a substrate. The work generated by the actuator surface in response to humidity changes results in a change in the curvature of the substrate (FIG. 1D). By monitoring this change, the work and power densities of the actuator surface can be measured. In this aspect, the polyimide tape was chosen as the substrate because it provides high stiffness and elasticity, limited water responsiveness, and durability even after series of deformation cycles. The resulting bilayer structure unfolds at 90% RH (FIG. 1E), bends, and exhibits a cylindrical geometry at 20% RH (FIG. 1F).

One aspect provides a fluid responsive actuator comprising a plurality of fluid responsive elements. In this aspect, the fluid responsive elements have a tensile modulus larger than about 100 megapascals (MPa), wherein the fluid responsive elements are capable of generating a power-to-volume ratio sufficient to inject a drug from a syringe within an injection period from about 1 to about 60 seconds after exposure of the fluid responsive elements to a fluid.

The term "fluid responsive actuator" refers to an actuator comprising a fluid responsive material that exerts actuation force as a result of a change in its three-dimensional or two-dimensional shape resulting from perturbations to the ambient humidity or with natural or intentional fluctuations in environmental stimuli.

The term "fluid responsive actuator" refers to an actuator comprising a fluid responsive material that exerts actuation force as a result of a change in its three-dimensional or two-dimensional shape resulting from perturbations to the ambient humidity or with natural or intentional fluctuations in environmental stimuli.

The term "fluid responsive element" refers to an element that can generate energy after contact with fluid by, for example, rapid expansion. A fluid responsive element can include one or more of spores (e.g., *Bacillus* spores), cellophane, paper, cellulose, regenerated cellulose combined with an adhesive and optionally deposited on a substrate as described herein. Layers of fluid responsive elements can be combined (e.g., in stacks) and connected (e.g., attached with an adhesive) to form a fluid responsive actuator. A fluid responsive element can include one or more fluid responsive elements.

The term "injection period" refers to the period of time measured from when a fluid contacts the fluid response elements until some or all of a drug in an injector is expelled from the fluid responsive actuator or fluid responsive injector.

In another aspect, the injection period is from about 1 to about 60 seconds, about 5 to about 30 seconds, about 10 seconds, or about 15 seconds. The injection period can be adjusted, for example, by the design of the fluid responsive actuator as described herein (e.g., speed of exposure to fluid, fluid channels, stacking of fluid responsive elements, etc.).

In one aspect, the power-to-volume ratio is at least about 10 kW $m^{-3}$, 20, 50, 100, 500, 1000, 2000, 5000, and 10000 kW $m^{-3}$. In another aspect, the power-to-volume ratio is about 3000 to about 8000 kW $m^{-3}$.

Optionally, the fluid responsive actuators comprise a substrate (e.g., polyimide). The fluid responsive elements can be deposited on to the substrate with or without an adhesive as described herein.

In another aspect, the fluid responsive elements comprise one or more of spores, cellophane, paper, cellulose, and regenerated cellulose. The term "spore" (aka endospores) refers to a dormant form of vegetative bacteria from species such as *Bacillus* and *Clostridium*. In this aspect, the spores can be selected from the group consisting of *Bacillus subtilis, Bacillus thuringiensis* and *Bacillus cereus.*

In another aspect, the fluid responsive elements further comprise a confining material to reduce lateral movement of the fluid responsive elements. The confining material can comprise an adhesive. In one aspect, the adhesive is a water-soluble adhesive (e.g., poly(vinyl acetate).

In another aspect, the fluid response elements and adhesive form a fluid response element matrix, and channels are formed within the fluid response matrix. The term "channels" refers to a tube, groove, change in thickness, roughness, divot, pattern, etching, curvature or similar structure in a material that is capable of directing, diverting, accumulating, or changing the direction of a fluid. In another aspect, the channels are aligned with at least one substrate channel formed in the substrate.

In another aspect, the fluid responsive elements have a shape selected from the group consisting of a cylinder, a prism, and an amorphous shape having a cross section perpendicular to the length of the actuator in the direction of movement of the fluid responsive elements between about 9 $mm^2$ and 2800 $mm^2$.

In a further aspect, the shape has a cross section perpendicular to the length of the actuator in the direction of movement of the fluid responsive elements of at least about 9 $mm^2$ to about 200 $mm^2$ for a drug with a viscosity of less than 20 cP. In yet another aspect, the shape has a cross section perpendicular to the length of the actuator in the direction of movement of the fluid responsive elements of at least about 100 $mm^2$ to about 1000 $mm^2$ for a drug with a viscosity of greater than or equal to 20 cP.

In another aspect, each of the plurality of fluid responsive elements comprises a layer, and the layers are stacked to form a layered architecture. In yet another aspect, the layers can be connected, bonded, or attached to each other with, for example, an adhesive or by any other suitable means. In a further aspect, the variations (e.g., variations in thickness, roughness, and patterning) in the layers form channels. Variations include, but are not limited to, punched or laser-cut channels.

Aspects described herein provides a fluid responsive injector comprising a fluid chamber, a fluid responsive actuator, and a release mechanism for controlling contact between a fluid in the fluid chamber and the fluid response actuator, a drug chamber having a discharge orifice, and a movable fluid-tight barrier positioned between the fluid responsive actuator and the drug chamber, wherein after the release mechanism permits contact between the fluid from the fluid chamber and the fluid responsive actuator, the fluid responsive actuator expands and exerts sufficient force on the barrier to push a drug in the drug chamber through a needle that has been affixed to the discharge orifice within an injection period from about 1 to about 60 seconds after exposure of the fluid responsive actuator to a fluid. In this aspect, the injection period can be from about 5 to about 60 seconds, about 5 to about 30 seconds, about 10 seconds, or about 15 seconds. In one aspect, the fluid responsive injector further comprises the needle.

Figure 6A:
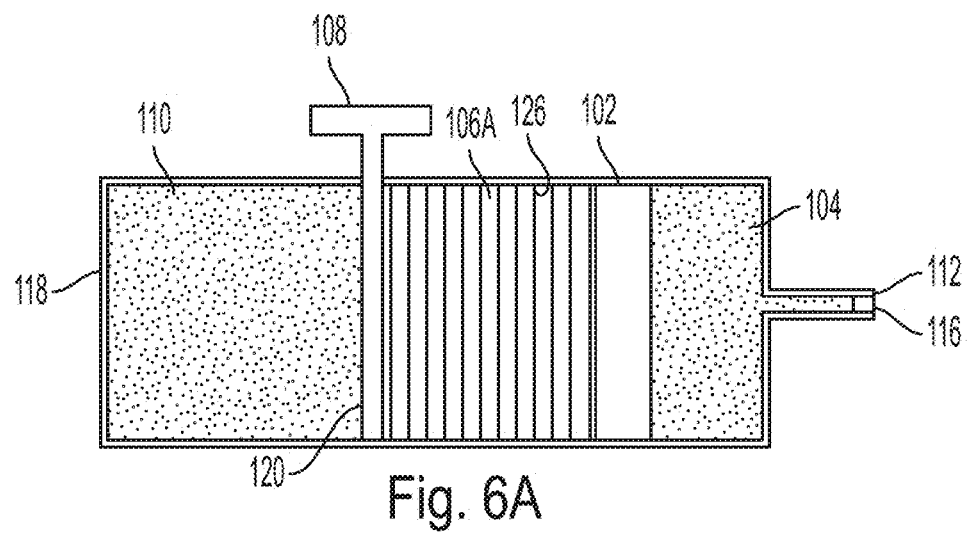
Figure 6B:
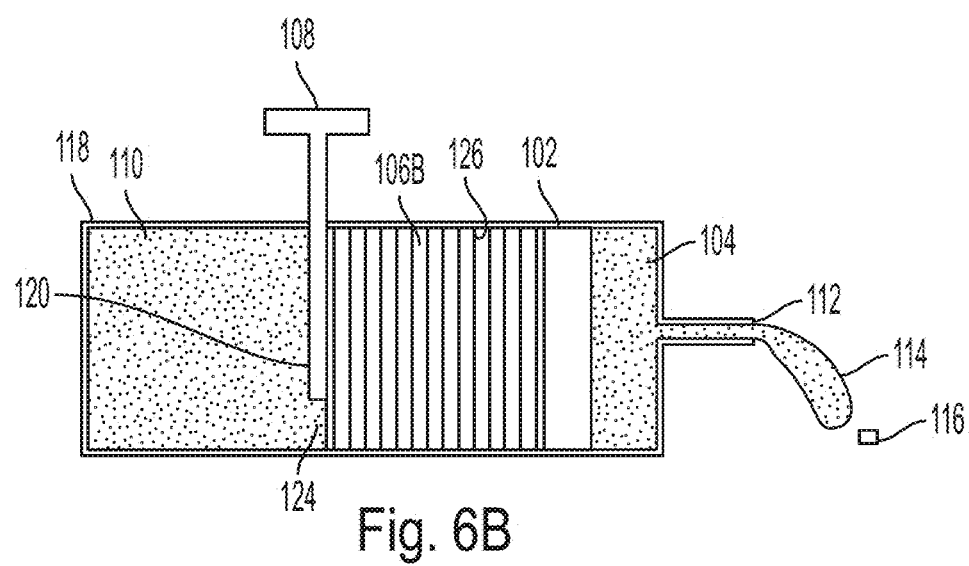

The term "movable fluid-tight barrier" refers, for example, a plunger (e.g., FIG. 6A, plunger 102) or similar device or mechanism that can apply a force to push a drug in the drug chamber out of an injector through, for example, a needle.

It is to be understood that the injectors described herein could incorporate aspects that are used in spring loaded injectors. These aspects include, for example, a housing that contains the actuator, a fluid that activates the actuator, a drug containing vessel, a push button or other trigger mechanisms that can be activated by a finger can be placed on the housing, with the button coupled to a trigger mechanism that releases the fluid to activate the actuator, and a latch mechanism that guards the actuator from pressing against the plunger prior to device activation, and a mechanism that removes the guard so that the actuator mechanically engages the plunger. The injector assembly could also incorporate a retractable needle cover that exposes the needle upon retraction to protect the patient from injury with the sharp needle. The housing can feature a window to show the drug compartment, and sensors and indicators that present visual and/or audible information to indicate the triggering of drug injection and completion of the injection process.

In a further aspect, the fluid responsive actuator comprises a plurality of fluid responsive elements have a tensile modulus larger than about 100 megapascals (MPa). In another aspect, the fluid responsive elements can generate a power-to-volume ratio of at least about 10, 20, 50, 100, 500, 1000, 2000, 5000, and 100,000 kW m$^{-3}$. In another aspect, the power-to-mass ratio is about 3 to about 8 kW kg$^{-1}$.

In another aspect, the fluid responsive elements include at least one substrate (e.g., polyimide). The fluid responsive elements can be deposited on to the substrate with or without an adhesive as described herein.

In another aspect, the fluid responsive actuator comprises comprise one or more of spores, cellophane, paper, cellulose, and regenerated cellulose. In this aspect, the spores can be selected from the group consisting of Bacillus subtilis, Bacillus thuringiensis and Bacillus cereus.

The fluid responsive elements can include a confining material to reduce lateral movement of the fluid responsive elements. The confining material can include an adhesive. The adhesive can be a water-soluble adhesive (e.g., poly (vinyl acetate).

The fluid response elements and adhesive can form a fluid response element matrix, and channels are formed within the fluid response matrix. The channels can be aligned with at least one substrate channel formed in the substrate.

In another aspect, the fluid responsive elements have a shape selected from the group consisting of a cylinder, a prism, and an amorphous shape having a cross section perpendicular to the length of the actuator in the direction of movement of the fluid responsive elements between about 9 mm$^2$ and 2800 mm$^2$.

In a further aspect, the shape has a cross section perpendicular to the length of the actuator in the direction of movement of the fluid responsive elements of at least about 9 mm$^2$ to about 200 mm$^2$ for a drug with a viscosity of less than 20 cP. In yet another aspect, the shape has a cross section perpendicular to the length of the actuator in the direction of movement of the fluid responsive elements of at least about 100 mm$^2$ to about 1000 mm$^2$ for a drug with a viscosity of greater than or equal to 20 cP.

In yet another aspect, each of the plurality of fluid responsive elements comprises a layer, and the layers are stacked to form a layered architecture. The layers can optionally be bonded, connected, or attached to each other with, for example, an adhesive. Variations (e.g., thickness, roughness, and patterning) in the layers can form channels. The fluid can be selected from the group consisting of water, saline, buffer, or any suitable liquid pharmaceutical or cosmetic carrier. The fluid responsive injector can include a drug ejection regulator (e.g., plug or valve). In addition, the fluid responsive injector can include a drug (e.g., high molecular weight molecules, biologics). Alternatively, the drug can be supplied to the fluid responsive injector prior to use. The drug can have a viscosity from about 1 cP to about 30 cP. The power and work densities for the actuators described herein are capable of injecting drugs with viscosities of up to 200 cP or 1000 cP and in a volume of up to about 2 ml of a liquid carrier in a short period of time (e.g., about 5 to 60 seconds).

Further aspects provide methods of injecting a drug into a patient in need of an injection of the drug comprising activating the release mechanism of the fluid responsive injectors described herein. In this aspect, the fluid responsive injector further comprises a drug, the fluid responsive elements are exposed to a fluid, and the drug is injected into the patient within an injection period. The term "patient" refers to a human or animal in need of or desirous of an injection of a drug for therapeutic or cosmetic purposes. In another aspect, the term "drug" refers to a substance or material that can be used for a therapeutic or cosmetic purpose. Drugs can include high molecular weight molecules such as biologics. In this aspect, the injection period can be from about 1 to about 60 seconds, about 5 to about 60 seconds, about 5 to about 30 seconds, about 10 seconds, or about 15 seconds In another aspect, the fluid responsive actuator further comprises at least one substrate wherein the fluid responsive elements can be deposited on the substrate (e.g., polyimide). In yet another aspect, the fluid responsive actuator comprises one or more of spores (e.g., Bacillus subtilis, Bacillus thuringiensis and Bacillus cereus), cellophane, paper, cellulose, and regenerated cellulose. The fluid responsive elements can further comprise a confining material to reduce lateral movement of the fluid responsive elements.

The confining material can comprise an adhesive. The adhesive can be a water-soluble adhesive (e.g., poly(vinyl acetate)). In another aspect, the fluid response elements and adhesive can form a fluid response element matrix, and channels are formed within the fluid response matrix. The fluid can be selected from the group consisting of water, saline, buffer, or any suitable liquid pharmaceutical or cosmetic carrier. The fluid responsive injector can include a drug ejection regulator (e.g., plug or valve).

In addition, the fluid responsive injector can include a drug. Alternatively, the drug can be supplied to the fluid responsive injector prior to use. The drug can be a high molecular weight drug and have a viscosity from about 30 cP to about 200 cP. In another aspect, the power-to-volume ratio is at least about 10 kW m$^{-3}$. In another aspect, the fluid responsive elements have a tensile modulus larger than about 100 megapascals (MPa).

In another aspect, the water-responsive actuator material is packaged in a low relative humidity environment, preferably below 50% relative humidity, to maximize the range of motion upon activation. To prevent the water-responsive actuator material from absorbing moisture after manufacturing, a moisture barrier film can be used to cover the packaging materials.

In another aspect, the drug is replaced with fluids used in cosmetic injections, including fillers. In another aspect, the injector is used to for subcutaneous and/or intramuscular injections.

For applications in pen type auto-injectors (also known as pen injectors), large physical dimensions could affect user comfort and handling. To reduce the overall length of an injector incorporating a fluid-responsive actuator, the drug filled syringe or vessel could be placed in hollow region formed in the fluid-responsive actuator near the end of the actuator facing the syringe needle, and a 'cup' shaped connector surrounding the syringe could mechanically couple said end of the actuator to the plunger.

EXAMPLES

Example 1—Humidity-Responsive Spore-Based Actuators

Figure 1A:
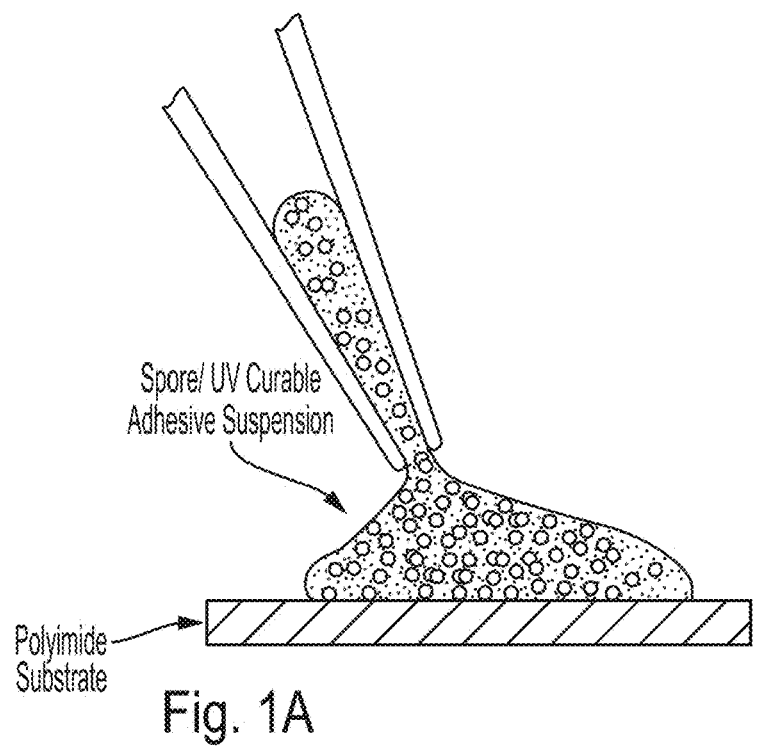
Figure 1B:
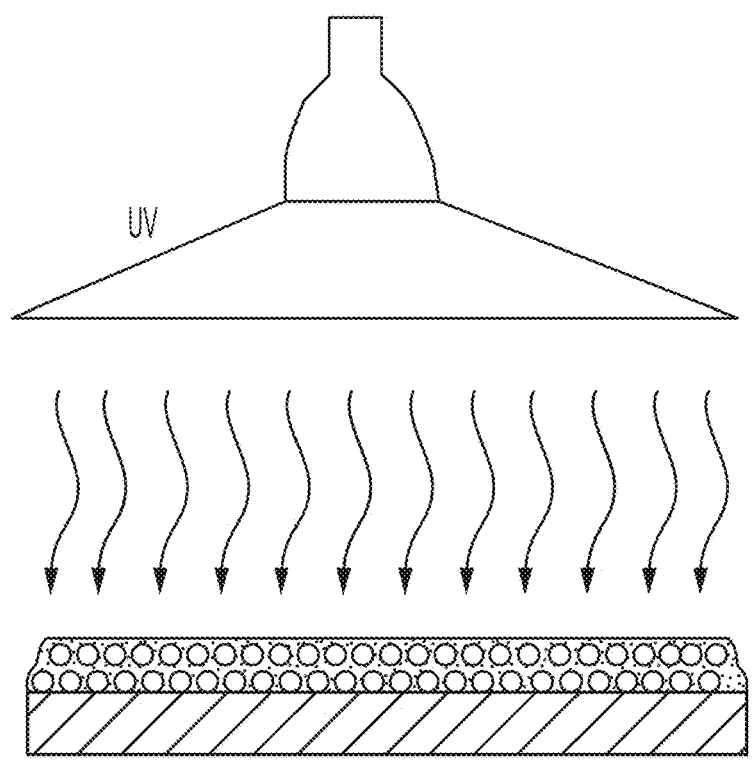
Figure 1C:
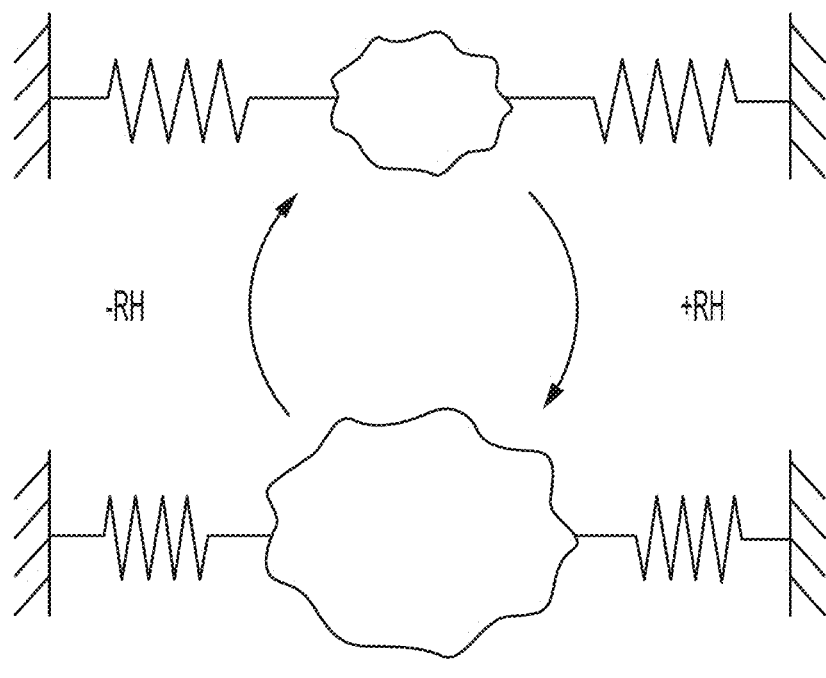
Figure 1D:
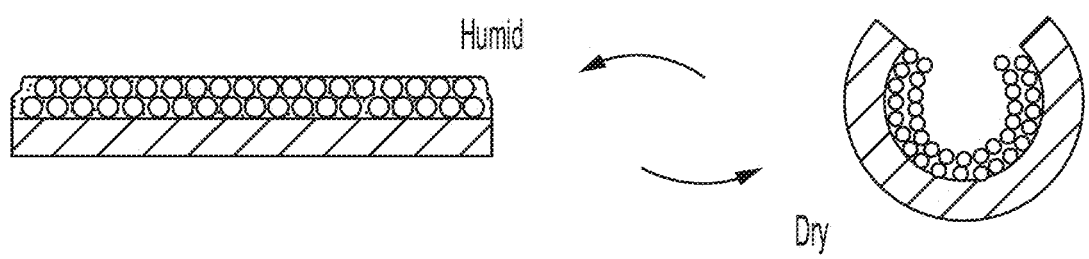
Figures 1E, 1F:
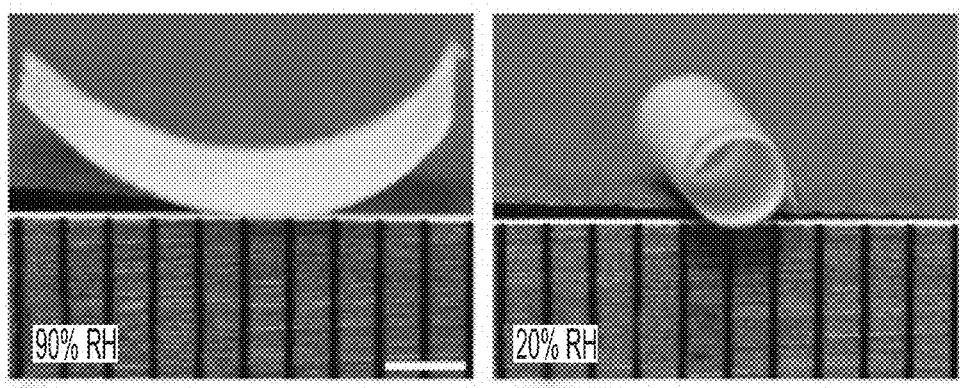
Figure 1G:
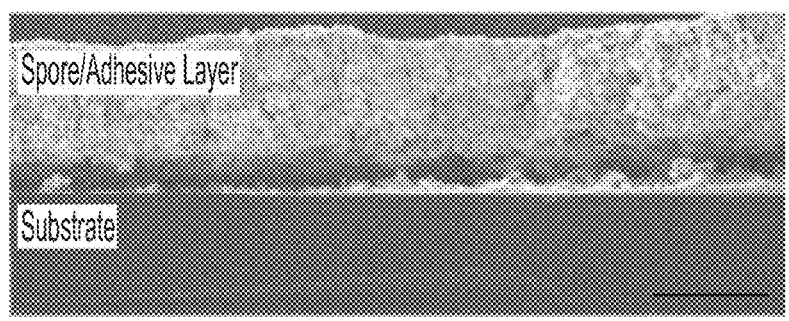
Figure 1H:
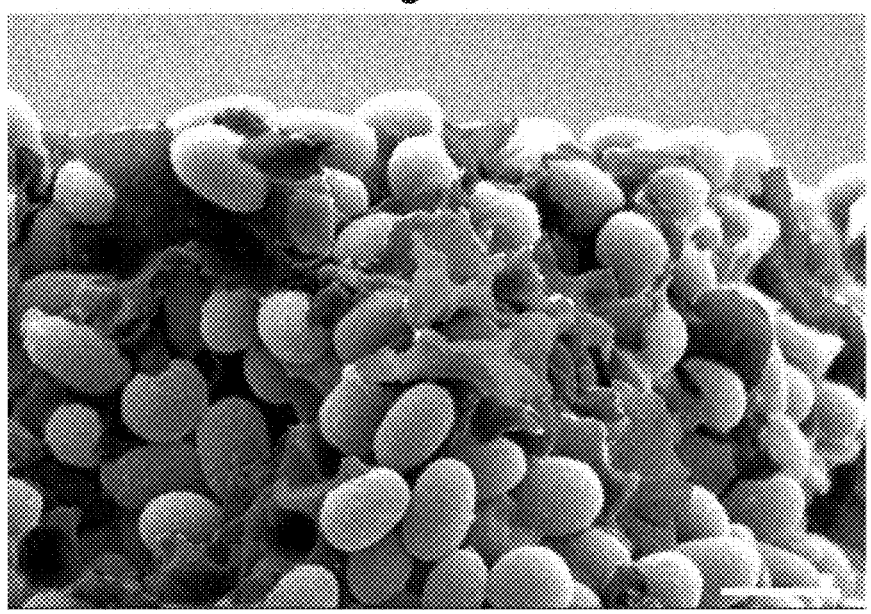
Figure 1I:
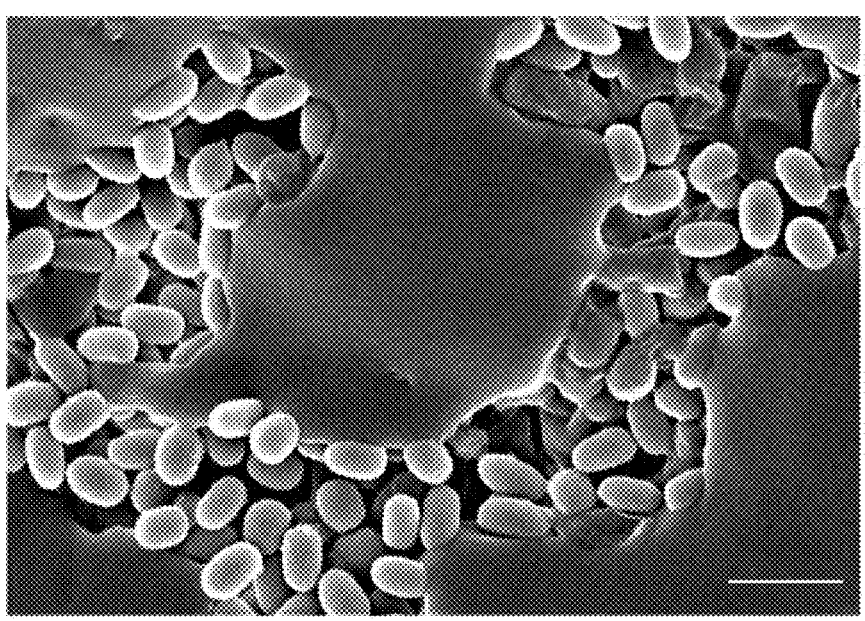

An exemplary spore/UV curable adhesive suspension in acetone was deposited on a polyimide substrate (FIG. 1A). The adhesive inside the suspension was cured with UV light and to form the actuator FIG. 1B). FIG. 1C illustrates bacterial spores changing shape and producing mechanical work in response to changes in relative humidity (RH). FIG. 1D shows the change in shape of an exemplary spore/adhesive actuator in response to changes in RH. The exemplary actuator containing spores and UV curable adhesives responds to humidity, causing a change of the curvature of the polyimide substrate. Photographs of the bilayer at 90% and 20% relative humidity are shown (FIGS. 1E and 1F). Scale bar is ~2 mm. A false colored SEM (scanning electron micrograph) of the cross section of the spore/adhesive layer—polyimide substrate is provided (FIG. 1G). Scale bar is ~25 µm. A top view 1H SEM of the spore—adhesive layer is shown (FIGS. 1H and 1I). Scale bar is ~1 µm. As shown, small adhesive islands form at the very top of the layer.

Example 2—Microstructures of the Actuators

Microstructures of actuators were analyzed using scanning electron microscopy (SEM). FIG. 1G shows the SEM image of the cross section of the substrate and the top layer. In this example, layer thicknesses of up to 30 µm was achieved without losing the integrity of the layer. The delamination seen in the image occurred when the sample was torn for SEM preparation. FIG. 1H shows a close-up cross section view of the actuator. In this example, the adhesive fills the voids between the spores. Small 'islands' of adhesives were observed on the top view (FIG. 1I) which shows that the adhesive and the spores tend to phase separate.

Without being bound by theory, it is believed that the curing and acetone evaporation happens so rapidly that the adhesive gets trapped inside the spore layers before the adhesive and spores completely separate. It is also believed that the adhesive accumulates on the top surface, and the dispersion of adhesive among the spores is not entirely homogeneous. This exemplary actuator is durable and functional, and most of the samples did not exhibit delamination or crack formation.

Example 3—Actuator Characterization

Figure 2A:
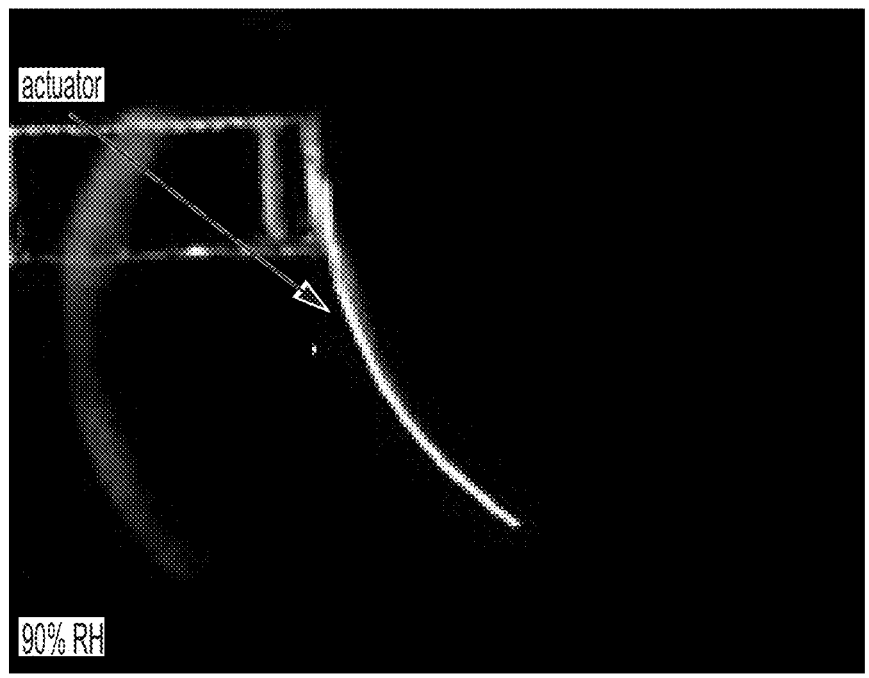
FIG. 2F illustrates the reversibility of the exemplary actuator devices under repeated stimulus.
Figure 2B:
Figure 2C:
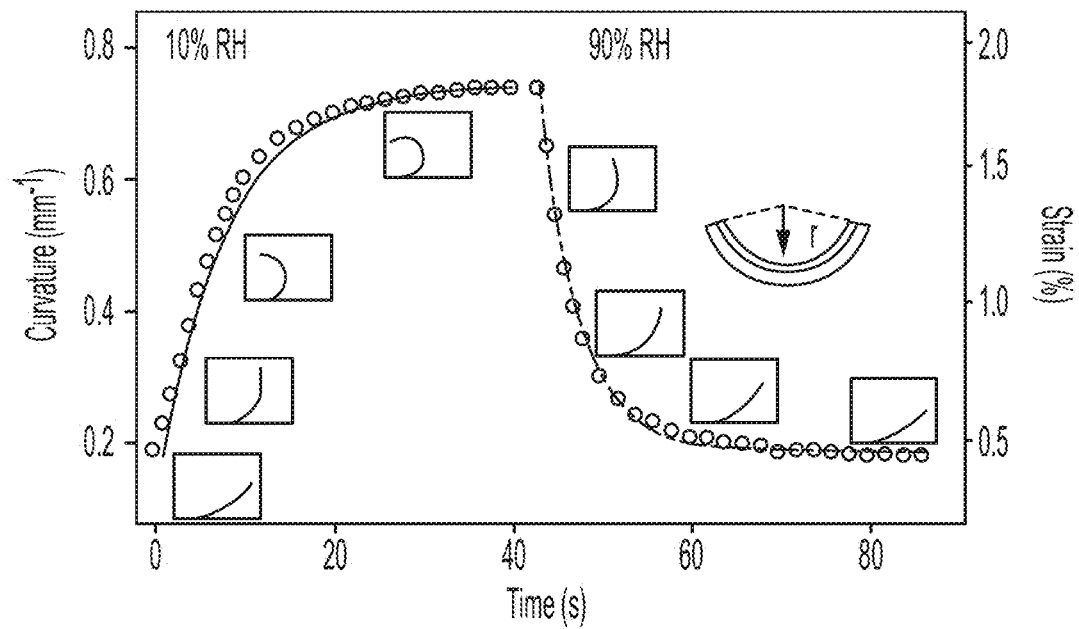

FIGS. 2A through 2F characterize actuator devices by monitoring their curvature when relative humidity was alternated between 90% RH and 10% RH at 23° C. The dimensions of the samples used for characterization were 6 mm×6 mm with a polyimide substrate thickness of 25.4 µm and a Young's Modulus of 2.5 GPa. Actuator device bending was recorded with a camera (FIG. 2A and FIG. 2B) to obtain the radius of curvature of the sample at each frame (FIG. 2C). Work density is the work produced by a unit volume of the actuator and can be calculated by dividing the strain energy of each sample by the total volume on it. Power density was obtained by dividing work density value to the time constant. Specific work and specific power were determined using the mass densities of spores and adhesives. The change in the curvature with respect to time was plotted and an exponential function was fit to the data to obtain the time constant. The strain energy was calculated using the radius of curvature, the length of the sample, the Young's Moduli of the spore/adhesive layer and polyimide substrate respectively, and the area moments of inertias.

Example 4—Characterization of the Spore Actuators

Figure 2D:
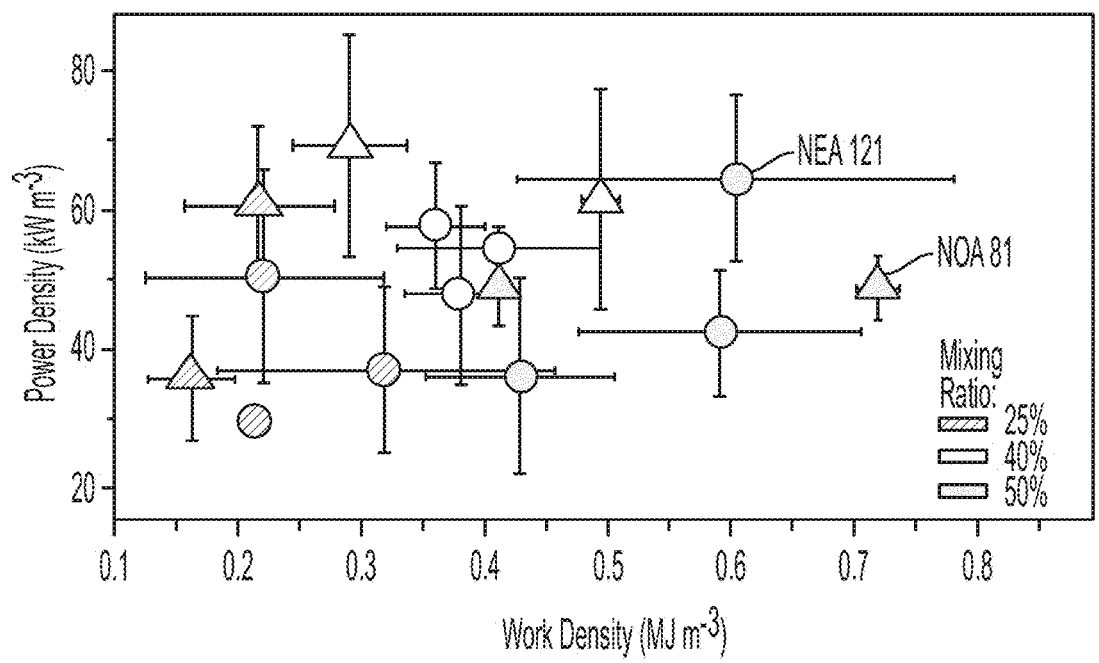

FIGS. 2A and 2B show the top view of an exemplary actuator in the chamber at 90% RH and 10% RH, respectively, with "r" indicating the radius of curvature. FIG. 2C illustrates the change in the curvature and strain of a sample during consecutive dehydration and hydration cycles. The radius of curvature was determined by numerically fitting a circle. The pictures along the curve show the contours of the test sample, obtained by tracing the edge of the samples in respective top-view photographs. An exponential curve was fit to the data points to obtain a time constant. Strain values were determined at neutral axis. Referring to FIG. 2D, the work and power densities of actuators containing NEA 121 and NOA 81 adhesives with varying adhesive content; 50%, 40%, and 25% were determined. Different data points with the same parameters correspond to different layer thicknesses. Error bars show the range of the typically three or two samples.

While the exemplary adhesive enables structural integrity of the actuators and provides adhesion between the spores, its concentration in the layer might influence actuation characteristics. Therefore, the effects of adhesive type and adhesive concentration on the work and power densities were measured. Samples containing NOA 81 and NEA 121 adhesives with varying adhesive contents were tested. FIG. 2D shows the work and power densities of different samples with NOA 81 and NEA 121, where the hatched, white, and black fill patters represent the mixing ratios 25%, 40%, and 50%, respectively. Trials were also performed. The mixing ratios were obtained by dividing the volume of the adhesive to the total volume of the actuator. The maximum work density and specific work was obtained using NOA 81 with 50% adhesive content. This value is at least one order of magnitude higher than synthetic fluid responsive polymers. In this aspect, the maximum power density and specific power was achieved at samples containing NOA 81 with 40% adhesive content.

Figure 2E:
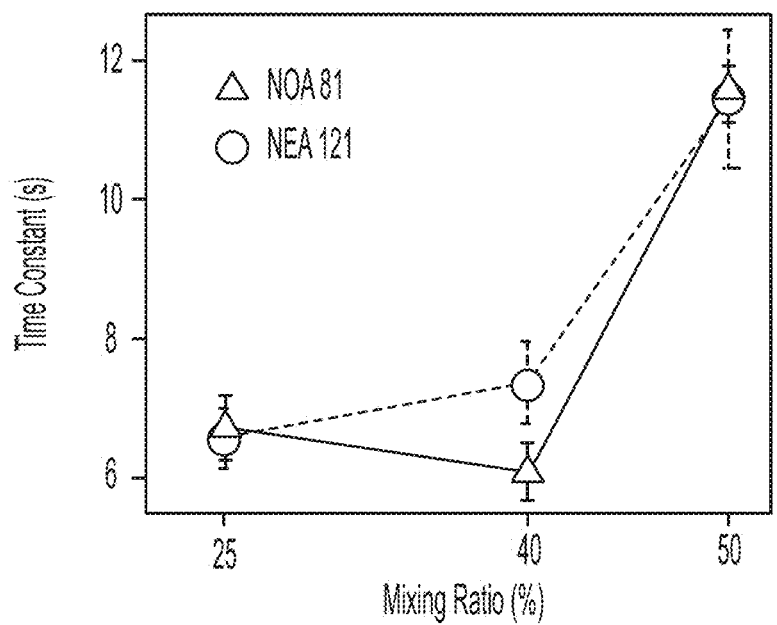

Without being bound by theory, it is believed that variation between samples with same parameters and materials can be explained by the random dispersion of the adhesive in spore layers. Samples with higher adhesive content tend to have higher work densities regardless of the adhesive type. It is believed that the voids between the spores were filled with the adhesive more densely, which can result in better energy transmission between spores and the substrate. The power densities, however, do not show the same trend. Increasing adhesive concentration may lead to increasing the strain energy, but it may result in slower actuation. (FIG. 2E). For example, there was a significant increase in the time constants when the mixing ratio was increased to 50%. This might be due to the adhesive filling the voids between spores which might be impeding the penetration of water molecules through the layer. One of skill in the art can adjust the adhesive content and other parameters to obtain the desired power density and time constant.

Figure 2F:
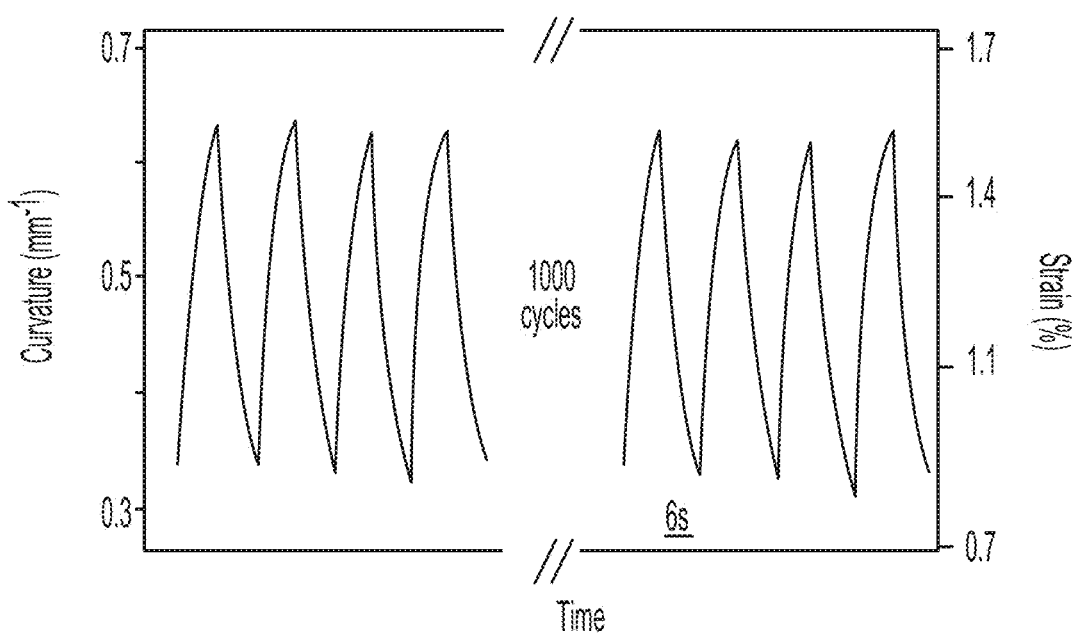

To investigate reversibility of these actuators under repeated stimulus, they were exposed to cyclical humidity changes for 1000 cycles (FIG. 2F). There was a negligible reduction in actuation strain, indicating that the actuators can be used repeatedly without significant loss of function.

Example 5—Schematic Representation of the Spore-Lithography Technique

In another aspect, an exemplary 2D 'flower' geometry was cut from the polyimide sheet using a laser cutter. An exemplary spore/UV curable adhesive suspension in acetone was deposited on the substrate. The UV-curable adhesive inside the suspension was cured. A UV mask enables patterning of the spore-adhesive layer on the substrate. The remaining uncured parts were removed with isopropyl alcohol. The resulting exemplary bioinspired 3D responsive actuator is a flower that blooms in response to humidity changes.

Scalable patterning of active hygroscopic surfaces can be used for applications requiring agile and sophisticated movements. In this aspect, the UV curability of the adhesives is combined with laser machining for "spore-lithography" patterning of bio-inspired responsive structures (FIG. 3A-D). Photolithography and laser machining are mature methods for mass production of decorative objects. Spore-lithography can be used for scalable fabrication of, for example, decorative hygroscopic actuators.

Figure 3A:
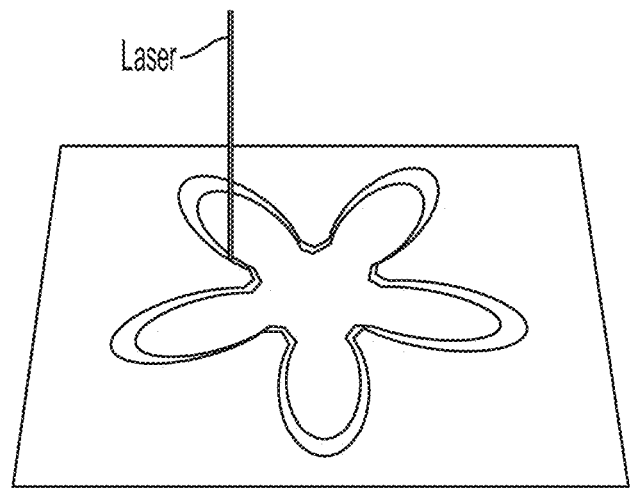
FIG. 3A illustrates an exemplary shape cut into a polyimide substrate by a laser.
Figure 3B:
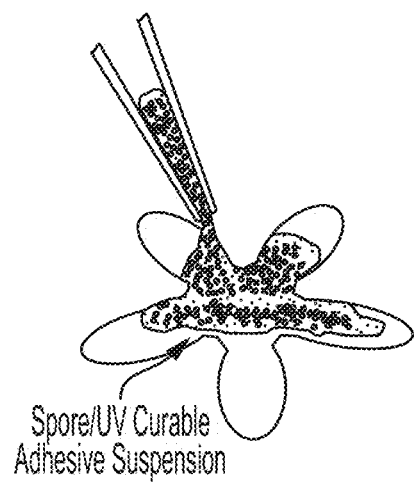
FIG. 3B illustrates deposition of an exemplary spore adhesive mixture on to the shaped polyimide substrate of FIG. 3A.
Figure 3C:
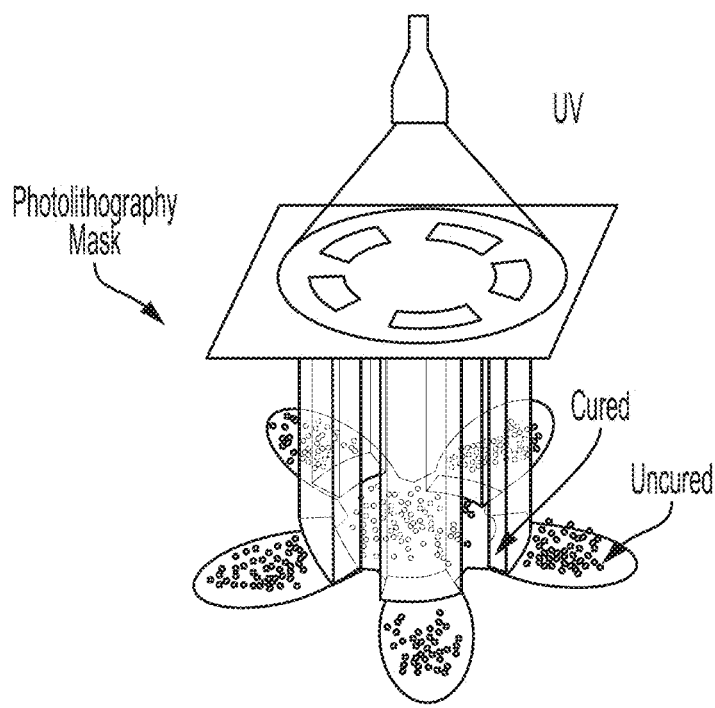
FIG. 3C illustrates the use of a photolithography mask between the ultraviolet (UV) light source, and the exemplary device of FIG. 3B to direct UV light to desired portions of the device.
Figure 3D:
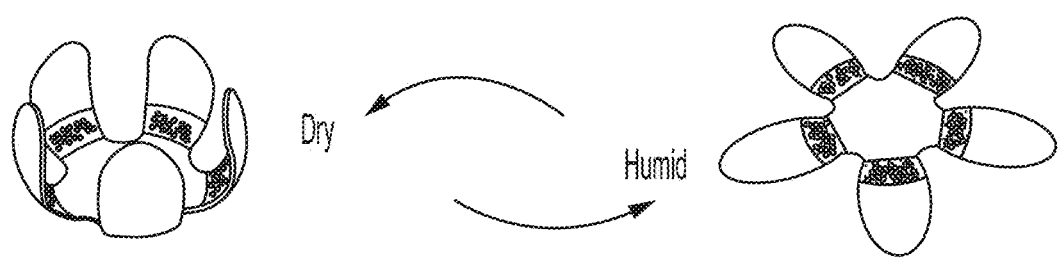
FIG. 3D illustrates the reversibility of actuator devices under dry (folder) and humid conditions;

In one aspect, the defined geometries and the lithography masks can be cut from a large sheet of polyimide film using a laser cutter (FIG. 3A). The spore/adhesive suspension can be pipetted on top of the substrate evenly (FIG. 3B). The mask can be aligned to the sample, and UV light can be applied (FIG. 3C). After UV exposure, the uncured parts can easily be removed by dipping the sample into isopropyl alcohol or using a swab. The resulting bio-inspired 3D responsive structures unfold when exposed to high humidity and fold back after drying (FIG. 3D).

To demonstrate the proof-of concept, 3D structures with flower (FIG. 4A), pyramid (FIG. 4B) and tulip shapes (FIG. 4C) were designed and fabricated. The active joints were patterned with photolithography, and enable folding and unfolding of the leaves upon changes in the relative humidity. The tulip was fabricated with a two-mask process. The first mask was for patterning the joints on the topside which enables the larger motion same as the flower and pyramid. The second mask was aligned to the opposite side for creating the out-of-axis curvature at the edges of the leaves.

The samples were placed inside a small chamber to alternate the relative humidity ("RH"). The RH in chamber varied between 20% to 80% within approximately 20 seconds. The unfolding and folding speed of the samples occurred within the same 20 second time frame, restoring to their initial position after every cycle. In the chamber, the folding/unfolding speed of the structures was limited by the speed of the humidity change in the chamber.

To demonstrate the rapid response, the samples were exposed to moisture with a humidifier. The experiments were conducted inside an environmentally controlled room with 20% RH at 25° C. The response of the samples to the moist air was immediate. The blowing speed of the moist air was very small, and did not effect unfolding.

Example 6—Flower, Pyramid, and Tulip

For flower and pyramid the actuator parts were patterned with a single mask photolithography. The curvature at the very edge of the tulip leaves was obtained with a second mask aligned to the backside. These actuators were placed inside a small chamber, and the relative humidity was changed from 80% to 20%.

Example 7—Extreme Power Densities of Water-Resistant Actuators

One factor limiting the actuation speed of fluid responsive actuators is the speed of vapor or fluid transport. In one aspect, using liquid water directly instead of water vapor to activate fluid responsive actuators can increase the actuation speed, and power density. However, humidity-responsive materials can be prone to degradation when they are in direct contact with a fluid such as water. For example, the function, shape, and characteristics of fluid responsive actuators can be affected by wetting and subsequent drying. In one aspect, water-resistant, yet water responsive materials can be used to take advantage of water-driven actuation. The spore-based actuators described in aspects herein preserve their integrity and reversible response even after repetitive immersion into water.

For example, spore coated tapes were dipped in water, (FIG. 5) and lifted them so that they can dry by air flow before the next cycle. In this aspect, upon immersion, the structures unfolded rapidly, in approximately 100 ms. Thus, water driven actuation can be about two orders of magnitude faster than humidity driven actuation (See FIG. 2E.) It is believed that water/vapor transport is the rate limiting step in humidity driven actuators rather than the transport kinetics of water within the actuator film. Upon drying, the samples recovered their curved shape, and the entire process was repeatable.

Example 8—Rapid, Reversible, Water-Driven Actuation

In this aspect, the spore-coated tape unfolded in 100 ms after it was completely submerged into the water at room temperature. Once the sample was lifted and dried with air flow, it regained its curved shape and was able to unfold repeatedly. The specific power of these exemplary spore-based actuators is between about 3.47 and 8.22 kW kg$^{-1}$.

Figure 5:
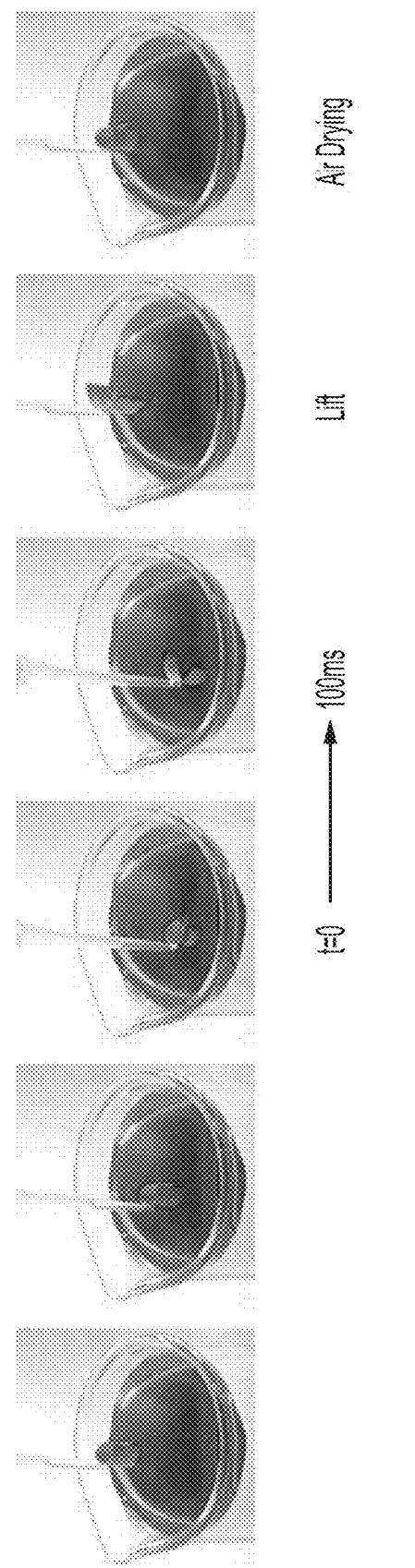

The rapid actuation demonstrated in FIG. 5 highlights a remarkable capacity of water driven actuation. Using the work densities determined in FIG. 2D and the time constant estimated from a film recording of the actuation, the specific power of spore-based actuators presented in aspects described herein is between about 3.47 and 8.22 kW kg$^{-1}$. These values are approximately two orders of magnitude higher than mammalian skeletal muscle, which falls between 50 and 284 W kg$^{-1}$.

In one aspect, humidity and water responsive materials provide actuators compatible with human environments with applications in, for example, robotics, energy harvesting, and adaptive architectures. In this aspect, *Bacillus subtilis* spores, which exhibit high work densities in the microscale experiments, are combined with UV-curable adhesives to create centimeter scale actuators. The UV curability of the adhesives, and scalable fabrication techniques described herein can achieve programmable actuation. In these aspect, water resistant surfaces can use direct liquid water as a stimulus for rapid actuation. For example, water responsive materials enable rapid response in the order of 100 ms. In addition, high specific power is achieved safely, without requiring invasive stimuli such as high electrical field or high temperatures. Combined with the demonstrated patterning method, the aspects described herein offer alternatives for soft robotics applications due to the pervasiveness and accessibility of water in the environment.

Example 9—Fabrication of the Actuators

In one aspect, spores are suspended in NEA 121 or NOA 81 adhesives diluted by 1:10 in an acetone solution. The suspension can be mixed in 1.5 ml vacutainer tube using a vortex mixer. Polyimide substrates can be cut from a 6 mm width roll (e.g., Cole Palmer) with a roller cutter. The dimensions of the substrates used in examples described herein were 6 mm×6 mm×0.0254 mm. The substrate can be placed on a microscope slide by manual pipetting. Acetone evaporates very quickly after deposition because of its high evaporation rate. Hence, in one aspect, the sample can be placed inside the UV chamber before acetone completely evaporates. The UV-curing can be conducted with a Splice Lamp which provides 2,500 µW/cm$^2$ light intensity. In this aspect, curing occurs in 1 min. In another aspect, the curing time depends on the thickness of the layer but even for layers more than 20 µm thick, 1 min of total curing time was sufficient for polymerization. During that time, the remaining acetone evaporated, and the samples were taken out of the UV chamber.

In this aspect, the samples were curved once the acetone evaporated completely. All these exemplary steps were conducted at room temperature and a RH of ~40%. In this aspect, one complete wetting and drying cycle before use improves the samples' performance. The total volume of the actuator layer can be calculated from the weight of each sample before and after deposition and the known densities of spores and adhesives. The known area of each sample can be used to determine the actuator thickness.

Example 10—Fabrication of Bio-Inspired 3D Responsive Structures with Spore Lithography The exemplary flower, pyramid and tulip shaped structures and photolithography masks were designed using Adobe Illustrator CS6 software. The exemplary geometries were cut from a 30 cm×30 cm polyimide film (Cole-Palmer) using a laser cutter. The exemplary lithography masks were machined from a 3 mm thick black acrylic piece using the same laser cutter system. In one aspect, acrylic can be used as mask material because it is easy to machine and a low-cost material. Standard photolithography tools, such as film or chromium masks, can also be utilized for smaller feature size requirements. The cut films with the unfolded flower, pyramid or tulip shapes can be placed on a polydimethylsiloxane (PDMS) coated acrylic holder. PDMS provides a sticky surface due to its electrostatic interaction with the polyimide tape and enables fixing of the sample for the alignment process. The film surface can be cleaned with ethanol, and the spore/adhesive suspension can be pipetted on the film uniformly.

The photolithography mask can be aligned to the substrate using guidance holes machined both on the holder and on the mask. The UV light can be applied with Splice Lamp which provides 2,500 µW/cm$^2$ intensity in the proximity mode. A spacer can be used to form a proximity gap of, for example, 50 µm. After 1 minute of UV exposure, the sample can be dipped inside the IPA for 20 seconds to remove the uncured parts. As a final step, these uncured parts can be cleaned with a wet swab to remove excess residue. A second mask process can be used for certain applications—(e.g., the tulip). In the tulip example, same procedure was applied to the backside of the substrate.

Example 11—Characterization of the Actuators

In one aspect, an exemplary chamber was built to vary humidity around the sample quickly and measure the responses of the samples. The exemplary chamber was made of acrylic parts machined with a laser cutter. The volume of the chamber was kept small to enable rapid humidity change. A stream of air was passed through the chamber and the RH of the air was controlled by mixing dry air provided by laboratory air source and humid air generated by passing laboratory air through a bubbler in a controlled fashion. A second source with lower flow rate was mixed with the main stream to set the minimum RH value to ~10% and maximum value to ~90%. A solenoid valve controlled by a custom LabVIEW interface was used to switch between the humid and dry states. A humidity sensor was placed next to the sample to monitor the humidity inside the chamber. The sensor was also connected to the same LabVIEW interface. The sample was attached to a vertical rod inside the chamber with a small piece of double-sided tape. The response of the actuators to the humidity change was recorded with a digital camera.

Example 12—Image Processing

In this aspect, the videos were 30 fps and with 640×480 resolution. The frame number was reduced using ImageJ and the video was processed using a custom script built in MATLAB. This custom script fits a circle to curved actuator images at each frame and measures the radii of curvature. The code is used to measure the curvature and the time constant of the respective spore samples. Initially, every frame was processed by the code and filtered to distinguish between background and substrate pixels. This filter used a threshold value to distinguish between the brightness of the material and the brightness of the background. The threshold value was determined based on the respective condition of the images. The remaining pixels were grouped into clusters to delineate regions of high pixel congregation, likely the substrate, from miscellaneous errata that was not removed by the filter. A circle was fit to the pixel clusters, and the radius of the substrate edge was extracted. The code produced images that superimposed the fit circle onto samples of the original images, to enable a final verification that the fit was proper. As the code processes every frame in the image sequence, it accumulates the varying radial values as the sample hydrates or dehydrates, expanding or contracting, respectively. These points form a data set which the code fit to an exponential curve using least squares method. Finally, the time constant of this curve was extracted, characterizing and comparing sample expansion or contraction rates.

Example 13—Submerging Experiment

In one aspect, a submerging experiment was conducted in an environmental room where the RH and temperature were maintained at 20% and 25° C., respectively. A sample with a rectangular geometry was prepared. In the dry state, the sample is curved and exhibits a cylindrical geometry. The sample was attached to a pipette tip which was connected to a motorized linear actuator to enable smooth soaking of the sample without any splashing. The actuator was soaked inside the distilled water and lifted back to the initial position. The liquid water on the actuator was wiped with a laboratory wiper and the actuator was dried with blowing dry air.

Example 14—Use of Spore Motor to Drive Injector Needle

Aspects described herein provide devices that can inject fluids, particularly for use in drug delivery, and the method of injection that is used in the device. The primary actuation mechanism of the device is a water responsive material adapted to exert force against a plunger in a syringe or syringe-like geometry. The actuation of the water responsive material is triggered by releasing water or other fluids that can be absorbed by the water responsive material. Certain water-responsive materials can generate large pressures upon mixing with water and this is advantageous for pushing materials (e.g., viscous drugs) through narrow injector needles. In particular, bacterial spores (*B. subtilis*) can generate pressures in excess of about 10 MPa, which is sufficient to push a fluid with a viscosity of about 30 cP in about 4 seconds through, for example, a 27 Gauge needle. Additional water-responsive materials that can be used for this purpose are cellulose based materials, hydrogels with Young's modulus exceeding about 100 MPa. In one aspect, spores of *Bacillus* genus (e.g., *B. subtilis* and *B. thuringiensis*) are suited for high pressure. *Bacillus* species can be genetically modified to alter water absorption and other properties. In embodiments, spores or other fluid-philic materials can generate pressures as high as 200 MPa or higher.

In another aspect, a high speed injection actuator comprises holes/channels to allow rapid transport of water to the water-responsive materials and rapid absorption of water. In one aspect, the diameter of these channels could range from about 100 nm to about a millimeter. In another aspect, the initial entry of water can be through a larger diameter channel.

In one aspect, the actuator material (e.g., water-responsive material) can be placed next to a resting surface so that only one end of the actuator will move upon water absorption. In this aspect, the other end will exert force against the plunger to, for example, inject the viscous fluid through a syringe needle. In another aspect, the mechanism to release water on demand could be a water filled pouch that is pierced by a sharp object. In yet another aspect, the piercing mechanism could be coupled to a button that is pressed by the user. In a further aspect, the piercing mechanism could be electrically controlled, and operated by a user-controlled switch. In this aspect, the intended user can be a patient or caregiver. Further water release mechanisms include melting of a material by heat, and light induced chemical changes.

In another aspect, the water activated injector device can incorporate a syringe needle. Further aspects provide a package or kit comprising the actuator, drug(s), water or other activating material, and a mechanism to release water or other activating materials. A convenient, rapid injector could avoid the use of wearable injectors that require the use of diluted drugs and deliver drug over a longer period of time. A quiet, convenient and rapid injector makes compliance with injection schedules easier.

FIGS. 6A and 6B show an exemplary injector that may be driven by a spore or other type of actuator in accordance with aspects described herein. In this aspect, water initially held in a chamber 118 is released through a gate by manipulation of a trigger 108. The trigger may be driven manually or automatically, such as by a spring or motor. The water 110 in the water chamber 118 contacts a water-responsive actuator by flowing through a passage 124 created by the movement of the gate. The water 110 enters the actuator 106A and causes it to expand 106B thereby pushing a plunger 102 to force a drug 104 through a needle 112. The drug may be held back initially by a plug 116 which may be forced out of the needle by the pressure generated and transmitted by the plunger 102 which originally comes from expansion of the actuator 106A/B. In another aspect, plug 116 can be replaced with a valve (e.g., pressure responsive valve) to controllably regulate the release of the drug. Note that the gate 120 may be completely withdrawn to fully expose the water. In another aspect, plug 116 can be replaced with a removable needle cap that the patient or caregiver removes prior to inserting the needle.

The exemplary injector of FIGS. 6A and 6B can be revised by the addition of a device to generate or store pressure of the water in the water chamber. FIGS. 7A and 7B illustrate only a single example in which a bladder 130 is filled with a hydraulic (or pneumatic) fluid concurrently with actuation of the gate 120. The bladder may be filled with a fluid by means of a hydraulic line 134. Alternatively, a compressible fluid such as air may be stored in the bladder or the bladder may contain a spring and be vented to draw air when the movement of the gate allows the water to reach the actuator 106A/B. Note that it is understood that the actuator embodiments can contain a channel network to distribute fluids around and within to reach each driver elements, such as spores. In alternative embodiments, cellophane is used instead of, or with, spores.

In the embodiments of FIGS. 6A through 7B, the actuator 106A/B may have ramifying (branching) passages to form a hierarchical hydraulic network that allows water to reach throughout the actuator and thereby minimize reliance on diffusion for the water to reach otherwise remote parts of the actuator 106A/B. Below, the present disclosure describes examples of such ramifying channels and how they can be manufactured conveniently with other elements of the actuator to form a completed actuator 106A/B.

In experiments described above, it was observed that spores can form two dimensional monolayers that can act as actuators. In aspects described herein, high speed of actuation can be achieved in three-dimensional systems based on spores or other high stiffness materials by rapid distribution of fluid throughout the system. This is achieved, for example, by providing a three-dimensional network of ramifying channels disposed throughout the actuator. In two-dimensional test examples, water molecules in a hydrating fluid (humid air or water) are directly absorbed by the spores. In three-dimensional structures, fluid diffuses through the material, and at a diffusion rate limited by the material, to reach spores buried deep in the structure. However, a distribution network as described herein allows the hydrating fluid to reach spores rapidly, with minimal reliance on diffusion.

For example, The time of diffusion scales according to the following relationship:

$\tau \sim h^2/D$ Here $\tau$ is the timescale of water transport within the spore based material, h is the distance over which water transport will take place and D is the diffusion constant.

Figure 7A:
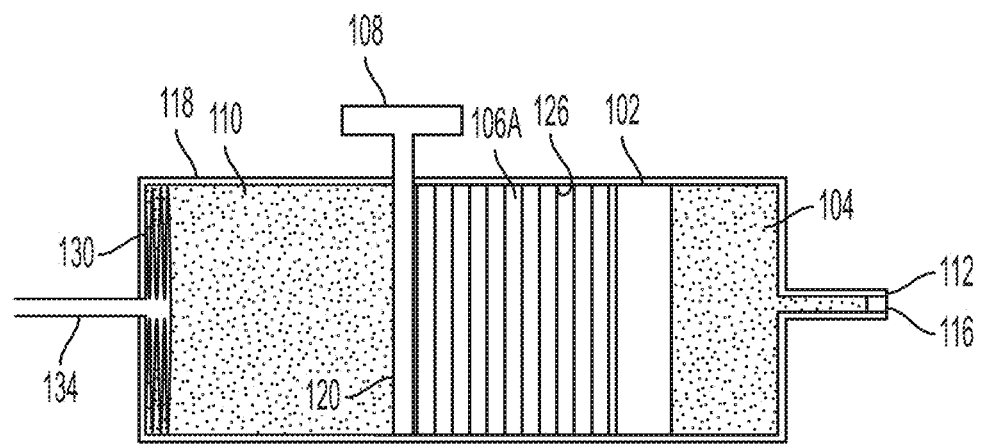
Figure 7B:
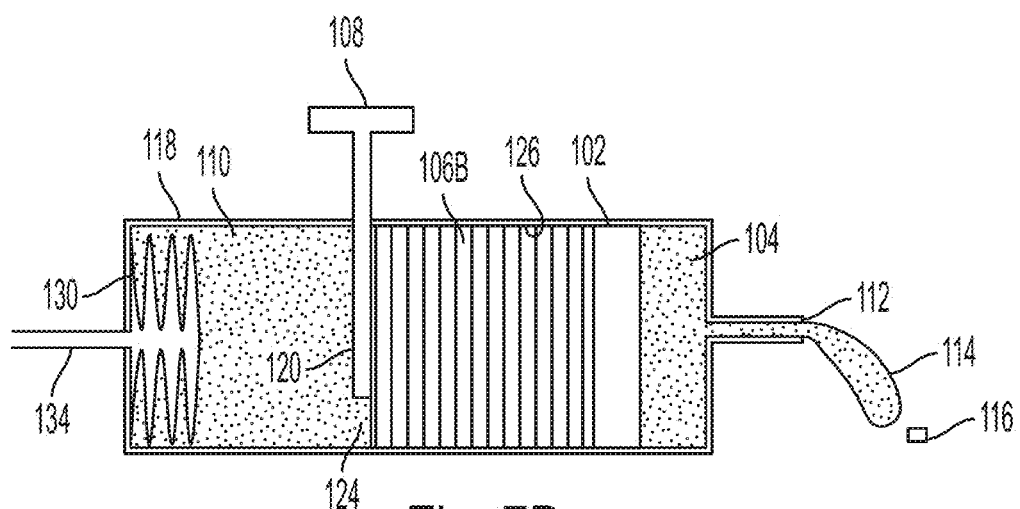
Figure 7C:
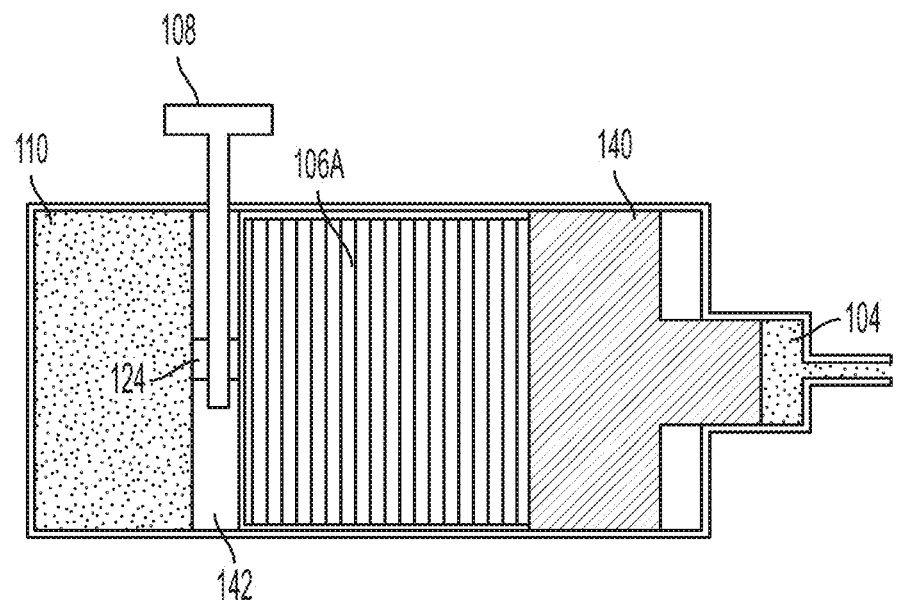

FIG. 7C illustrates some variations and a detail that may be employed in the embodiments of FIGS. 6A through 7B. An injector that may be driven by a spore or other type of actuator (e.g. cellophane) in accordance with aspects described herein. In this aspect, water 110 (or other fluid (e.g. alcohol) initially held in a chamber is released through a passage 124 by means of trigger 108. Here, note that the passage is in the center of a stop 142 that withstands the force of the expanding actuator 106A. Although not shown, it will be understood that the actuator may be perfused as described herein by means of an open or closed loop flow circuit driven by a pump or other means. Another feature shown in FIG. 7C is a device for pressure amplification. The sectional area of the actuator is greater than the sectional area of the drug chamber and the associated tip of the plunger so that a pressure amplification effect takes place. This means the pressure of the actuator need not be as great as the pressure in the drug chamber required for release of the drug through a needle in a desired period of time or flow rate.

In another aspect, the fluid is injected into the fluid responsive actuator by a first injector (e.g., water or fluid injector). This first injector can be a syringe so that the patient or the caregiver pushes the plunger to introduce the fluid into the fluid responsive actuator. Alternatively, the first injector can be a spring loaded or other pen type autoinjector that can be triggered to inject the fluid into the actuator. This pen type autoinjector can be activated by a button.

Figure 7D:
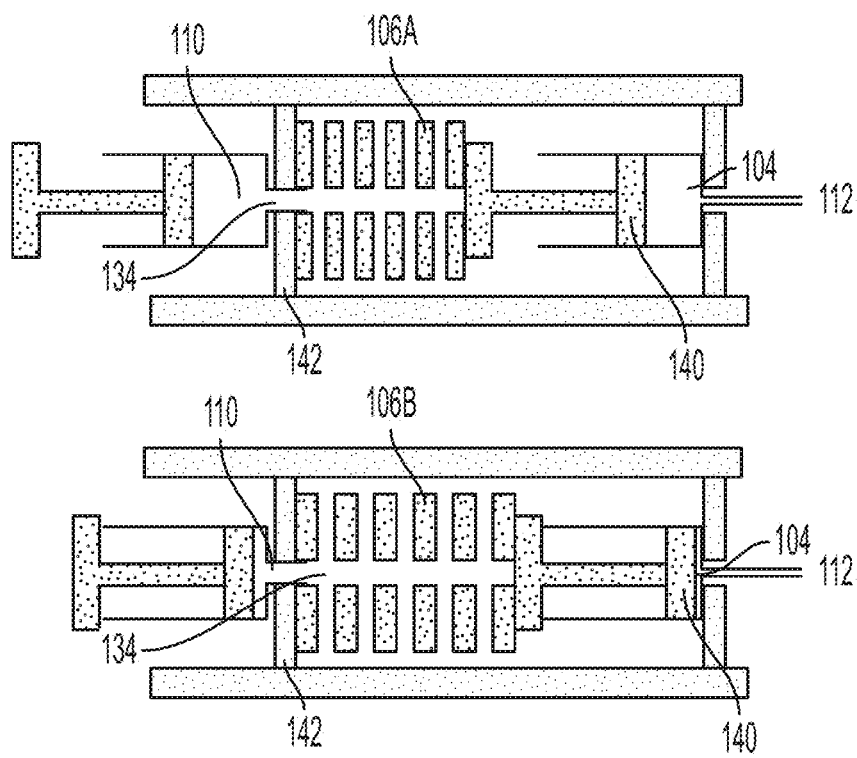

FIG. 7D illustrates this aspect using a water injector to introduce a fluid into the fluid responsive actuator. In this aspect, a user can activate a conventional syringe or functionally similar device to introduce a fluid (e.g., water, buffer, and saline) into the hygroscopic fluid responsive actuator triggering the actuator and pushing drug-containing fluid out of the drug injector as described herein. With reference to FIG. 7D (top), water 110 is in the water chamber. Plunger 140A can be pushed (FIG. 7D, bottom) and introduce water to actuator 106A. Actuator 106A/B can generate force (as described herein) triggered by water 110 which pushes plunger 140 and expels drug 104 from needle 112.

The water injector can be a conventional syringe, a pen type autoinjector (e.g., a spring driven autoinjector and a trigger mechanism to release the spring, wearable autoinjector) or any suitable injector. The trigger mechanism for the water injector can include a button that the user presses, as is typical for spring loaded auto-injectors.

In this aspect, the hygroscopic actuator can have channels in the fluid responsive elements that are filled by the water/fluid coming from the water injector. For example, the water injector can be directly coupled to channels such that the fluid coming out if the first injector flows through the channels in the hygroscopic actuator for rapid and efficient actuation.

Further to this aspect, the fluid responsive drug injector can be combined with sensors to indicate that the injection is complete. The water injector can also include retractable elements that hides the syringe needle as, for example, a safety feature.

Quadratic dependency of the water transport timescale with respect to the distance h means that the response time of a three-dimensional spore-based material can be extremely slow. To overcome this difficulty, spore-based materials having water transport channels can be used.

Figure 8A:
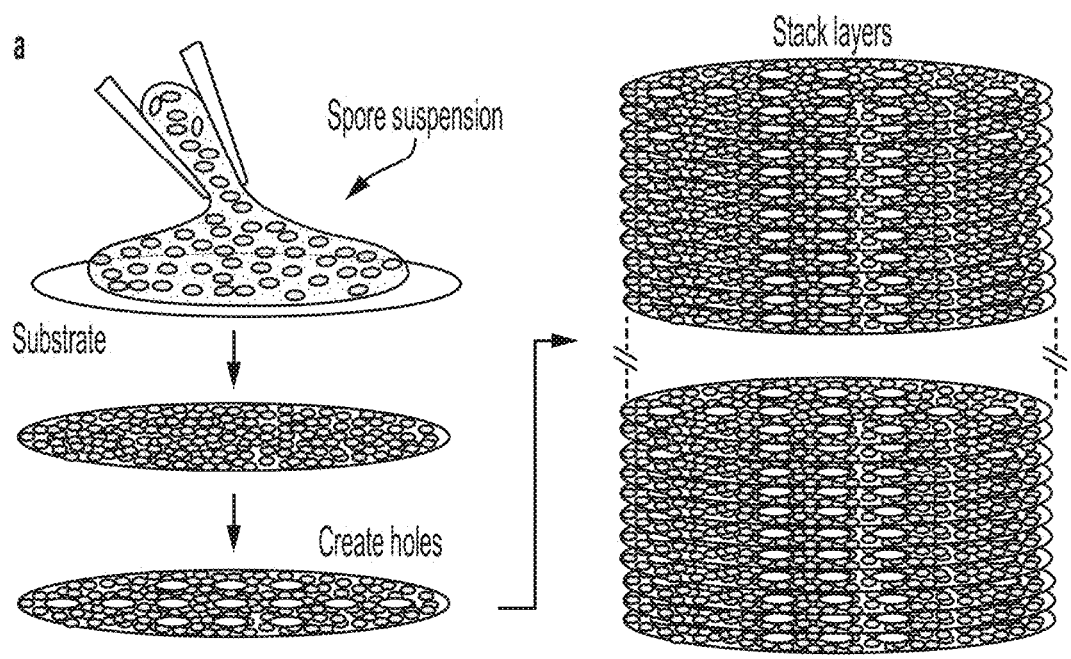
Figure 8B:
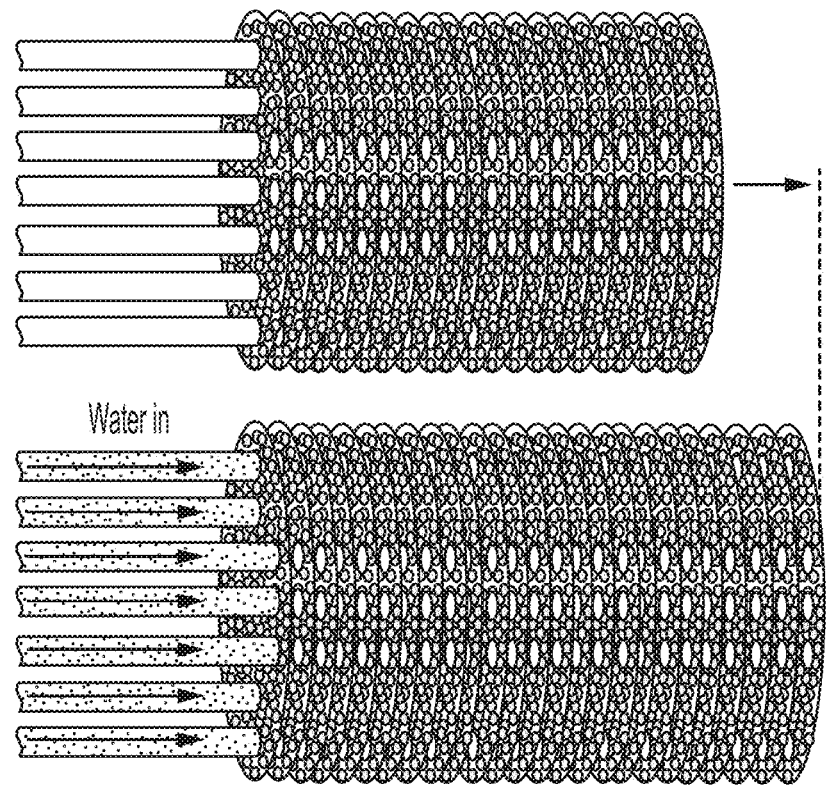
Figure 9A:
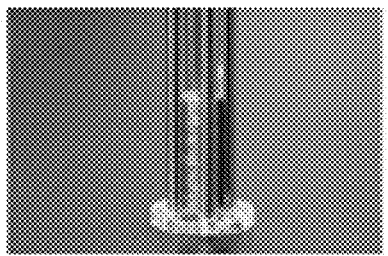
Figure 9C:
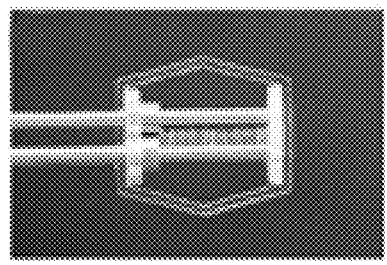
Figure 9E:
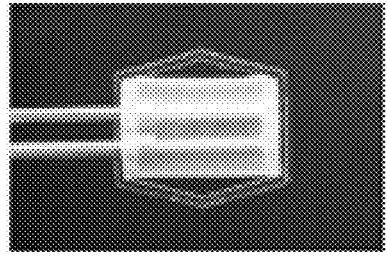
Figure 9B:
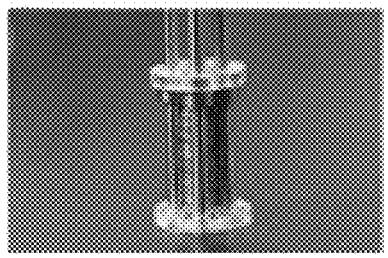
Figure 9D:
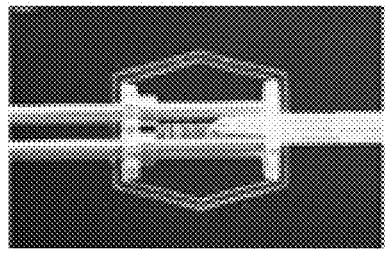
Figure 9F:
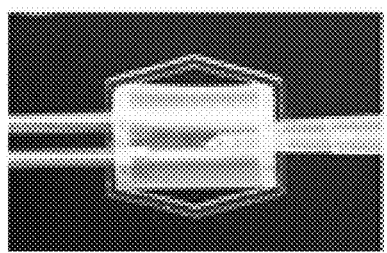

This basic concept is illustrated in FIGS. 8A and 8B. FIGS. 8A and 8B illustrate an exemplary actuator device having fluid responsive stacked layers of substrate with holes, a spore/adhesion suspension disposed thereon, and channels for distributing water through the holes in the stacked layers To test the basic functionality of spores stacked with substrates, an exemplary test sample was prepared by layering spores on Kapton® tapes and assembling them on top of each other as seen FIGS. 9A-9F. In this example, no channel network was provided except for the external surface of the stack. A piece of acrylic (hexagonal piece) is shown clamped down the entire stack and pipette tips provide inlet and outlet for humid and dry air. A sticky tape can be used to create a sealed enclosure, so that the air flowing from the inlet controls relative humidity. An exemplary finished test device is shown in FIG. 9F. This device is capable of actuation, demonstrating the feasibility and operability of the exemplary three-dimensional spore-based materials.

The exemplary configuration of FIGS. 8A and 8B has a travel distance of water on the order of 200 μm. The ratio of work density and response times for spores is power density. In one aspect, the work density of spores can be up to about 10 MJ/cubic meter and response time (i.e., injection period) during hydration can be about 0.4 seconds. The expansion ratio upon hydration (strain relative to the dry state) of spores was measured to be from about 6 percent to 11.7 percent. Chen et al., *Bacillus spores as building blocks for stimuli responsive materials and nanogenerators*, Nature Nanotechnology, Vol. 9, 137-141 (February 2014). This level of strain allows generating displacements of more than 1 cm when spore-based fluid-responsive actuators with lengths more than 10 cm, which can fit in a pen type injector and displace a plunger to deliver drug volumes in proportion to plunger cross-section area and plunger displacement. In different types of injectors, the dimensions of the drug compartment and the fluid responsive actuator can be adjusted match the actuator displacement to the displacement necessary to dispense a required volume of the drug.

Consequently, the power density (power-to-volume ratio) of spores can be up to about 25 MW/cubic meter upon hydration. The corresponding specific power can be determined by dividing the power density to mass density, which equals up to about 15 kW/kg, because the mass density of *Bacillus subtilis* spores in the dehydrated state is approximately 1.5 g/cubic centimeter. In another aspect, the response time (i.e., injection period) for a drug can be about 0.4, 1, 5, 10, 15, 25, 50, or 60 seconds or 1-60 seconds.

In another aspect, response time can be reduced in one aspect by creating in-plane microfluidic channels to convey hydrating fluid from the primary channels efficiently into each layer. In such embodiments, water delivered by vertical channels convects into the spore layers laterally via the microfluidic channels shortening the diffusion distance required compared to the configuration with only vertical channels. That is, these in-plane channels shorten the longest diffusion path required to reach remote portions of each layer, as illustrated in FIG. 9. In one aspect, channels can be formed using lithographically patterned molds comprising a channel hierarchy with channel widths starting from high to low. In another aspect, the channels can be formed in cellophane by laser cutting.

In another aspect, substrates, which essentially serve as scaffolds, can be thin to reduce overall strain of the actuator, for example. In a further aspect, the substrate material can have an elastic modulus that is comparable to or higher than the spore layer. In yet another aspect, the substrate is compatible with the machining process. Exemplary substrate materials include, but are not limited to, Kapton tapes, cured epoxies, mica sheets, and ultrathin glass sheets.

Spore adhesion: In one aspect, the structural integrity of spore layers depends on the adhesion between neighboring spores. Suitable materials for increasing spore adhesion include, but are not limited to, poly-1-lysine, adhesives (e.g., as described above), and polyvinyl acetate. In addition, spore adhesion can be increased by mechanical or other methods.

Figure 10A:
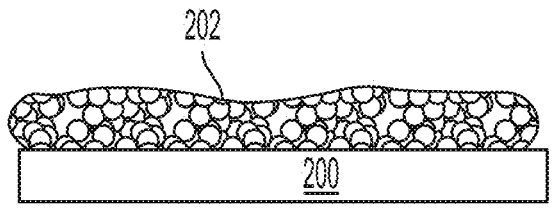
Figure 10B:
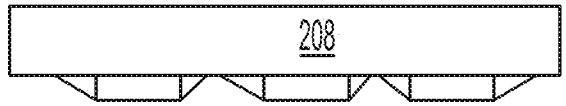
Figure 10C:
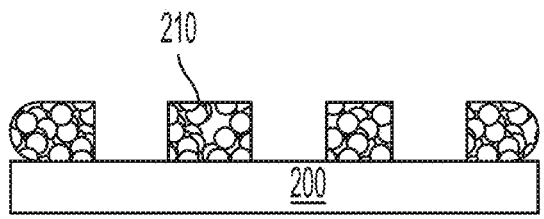
Figure 10D:
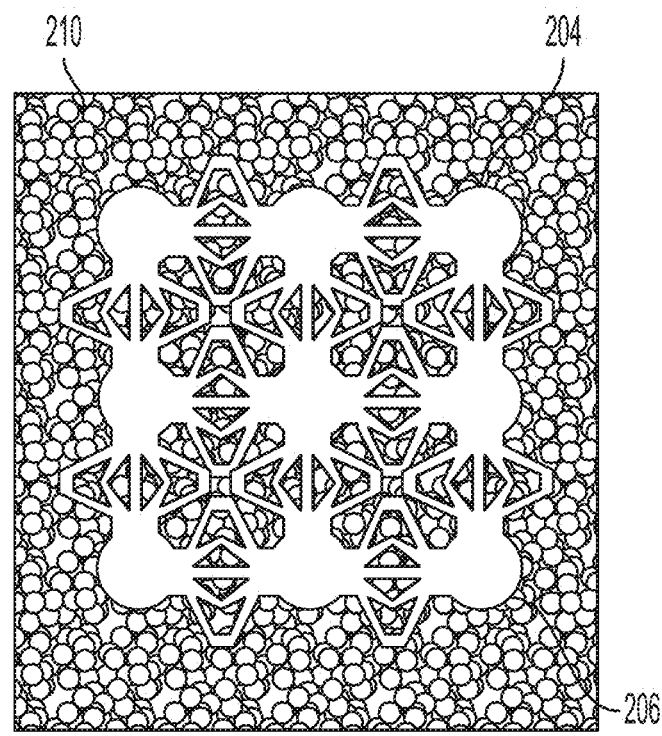
Figure 10E:
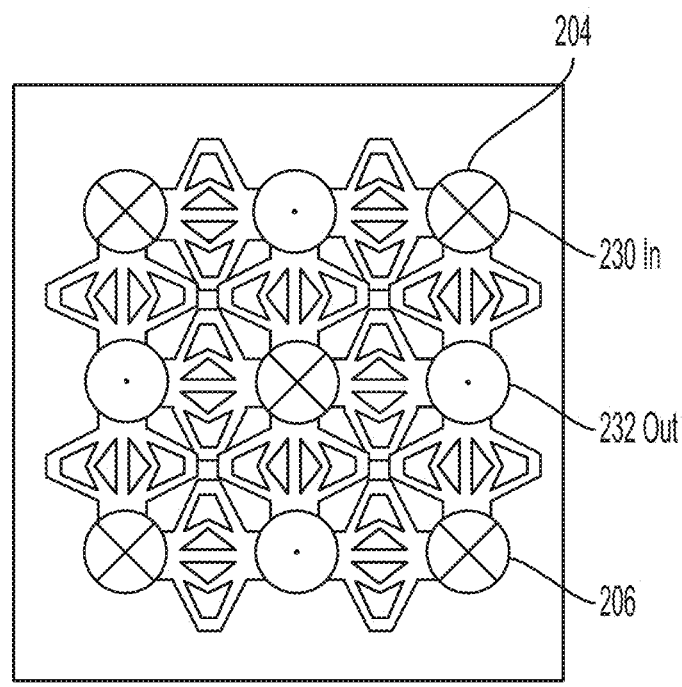

In one aspect, FIG. 10A shows an exemplary element of an actuator with a ramifying channel network. In this aspect, a layer of spores and adhesive 202 is laid on a substrate 200. The layer 202 may be molded by mold 208 as in FIG. 10B to form longitudinal and lateral channels that form a network as illustrated in FIG. 10E. Some longitudinal channels carry flow of water or other activating materials into the actuator (see 230) and some carry flow out (see 232). The substrate and molded layer of spores and adhesive 202 is shown in FIG. 10C. The layers are stacked to form a stack of layers as in 222. The layers may have the substrate (with holes punched through) or alternatively, the spores and adhesive 202 may be removed from the substrate and stacked. FIG. 10D shows the same channel network blackened in against layer of spores and adhesive 210. In FIG. 10D, molded bonded spore layer 201, channel network 204, and primary channels 206 are shown. The longitudinal channels shown in are more generally identified as primary channels 206. It will be evident that FIGS. 10A through 10F illustrate actuators with ramifying channels and a mechanism for supplying flow therethrough. In another aspect, the flow network can optionally be open such that the fluid entering the actuator can exit through openings (outlets). In this process, some of the fluid will be absorbed by the fluid responsive actuator. To prevent leakage to other parts of a device that the actuator is placed in, absorbent materials can cover the surface of the actuator. These absorbent materials are permeable to air but can trap the fluid. As shown in FIG. 10E, outlets can permit removal of trapped air filling channels 206 and channel network 204 and create channels for the fluid. In another aspect, the absorbent material can be replaced with a breathable fabric that serves as a barrier to the fluid but is permeable to air.

Figure 10F:
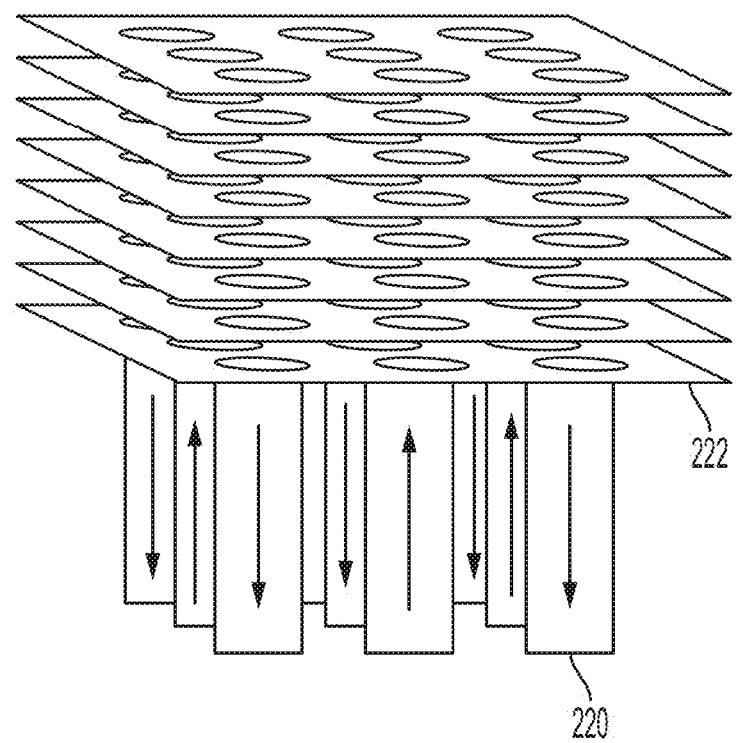

Note that in any of the embodiments, spores or cellophane or other suitable material may be used. Also, instead of water, alcohol may be substituted. Other materials will be evident to those of skill in the art. In FIG. 10F, multiple layers 222 and supply for primary channel 220 are shown. In FIG. 10F, hydrating fluid (water or humid air), for example, may be pumped into and out of the actuator.

Figures 11A, 11B:
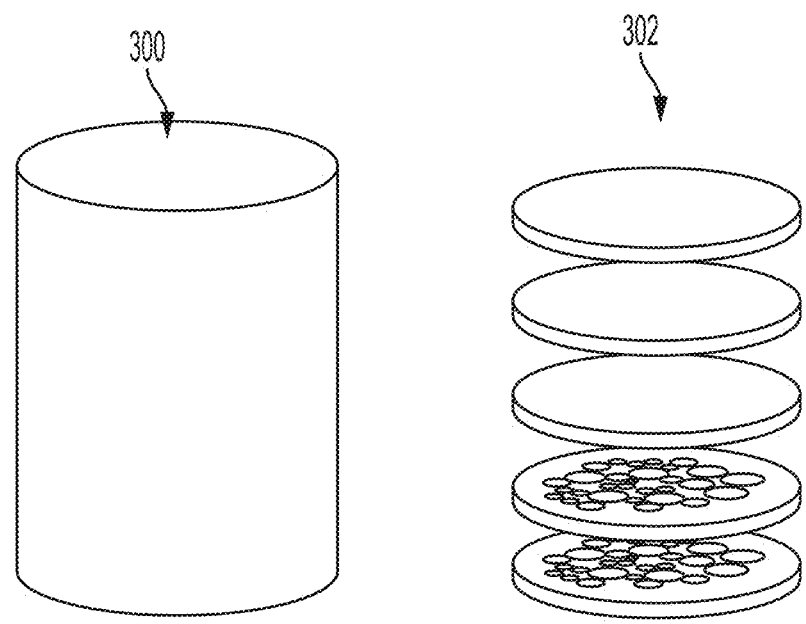

In the aspects illustrated in FIGS. 10A through 10F, the primary channels are not tapered. The aspects illustrated in FIGS. 11A through 11D utilize a channel network optimized in three dimensions and a method for making the same. FIG. 11A shows a monolithic actuator 300 with fractal channels therewithin. FIG. 11B show fractal channeling formed by layers 302 and illustrates an aspect where channel structures are formed by stacking layers with varying openings in each layer that align to form channels that taper progressively in the vertical direction as well as in the lateral directions. The layers can be 3D printed, using spores and adhesive, and the layers stacked as shown in FIG. 11B.

Figure 11C:
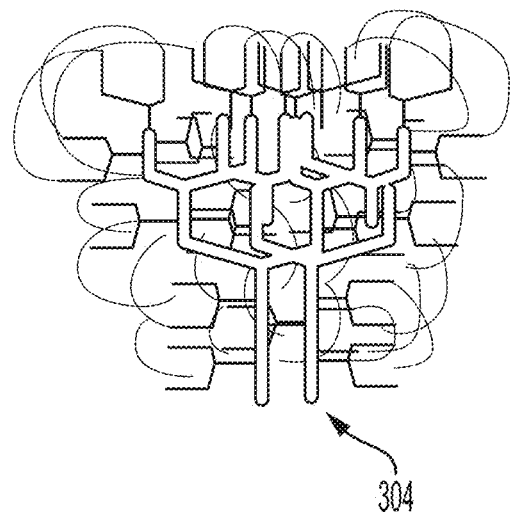
Figure 11D:
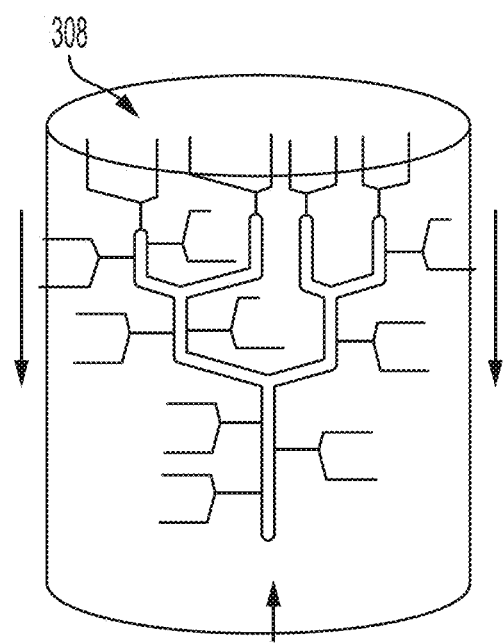

Alternatively, more complex biomorphic channel structures can be formed this way or with continuous 3D printing (i.e., a method which does not require a layer stacking process). FIGS. 11C and 11D illustrate an exemplary circulatory-type system forming an inflow and outflow (closed loop) flow network. FIG. 11C shows fractal channeling closed loop 304. FIG. 11D shows fractal channels open loop 308 and illustrates that the inflow and return channels need not be of the same type. In this aspect, a regular array of collection channels, such as annular gaps, could allow for a return flow while the outgoing channel network may be a fractal form of a circulatory system.

Design and optimization of the microfluidic network: In one aspect, the volume occupied by the fluidic network competes with the volume available for spores. Therefore, delivery of water with minimum fluidic network volume can be used to increase work density. However, using fluidic channels with small diameters can impose speed limitations due to fluidic resistance of these channels. In this aspect, an exemplary hierarchical network of fluidic channels can minimize fluidic network volume and increase speed. By analogy with the cardiovascular system, smaller channels can be at the front end where water reaches most of the spores. In this aspect, trapped air in the channels is minimized by using a network which provides hydrostatic pressure drop across all branches.

Figure 12:
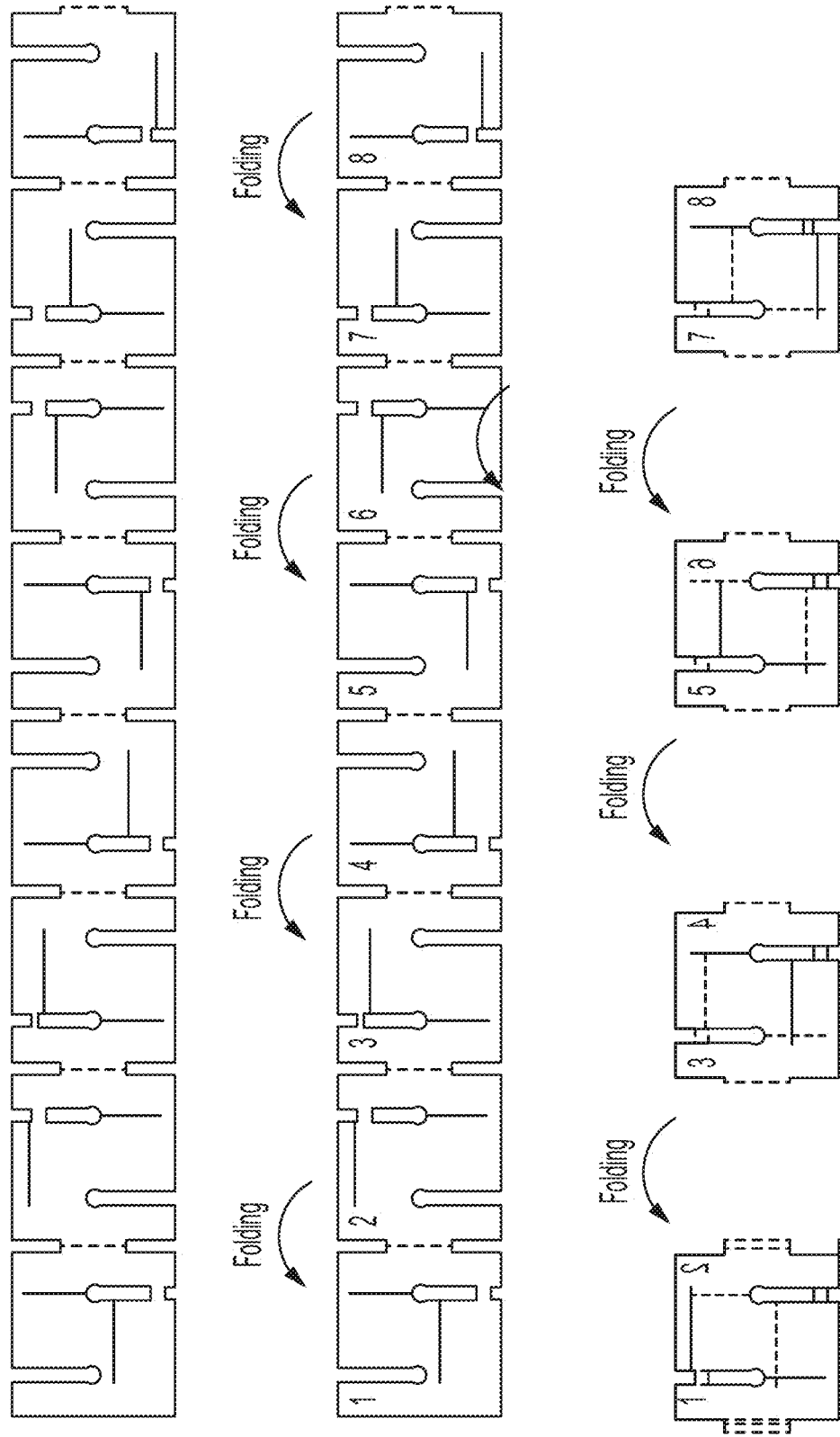

FIG. 12 shows lateral confinement 310 and fluid-phillic element 312. In this aspect, the exemplary actuator uses cellophane sheet. A sheet is punched to form transverse and through-channels when folded as indicated. Water can be pumped through the through-channels (the ones that are defined after folding that traverse the layers that stack upon folding). The folded elements can be stacked or continuously folded to form arbitrarily high stacks. The lateral channels, as discussed elsewhere, accelerate the take-up of water by the cellophane. The elastic modulus of the cellophane prevents it from expanding laterally (perpendicular direction to the longitudinal axis perpendicular to the layers) while the thickness expansion is cumulated to produce a high-power displacement longitudinally.

Figure 13:
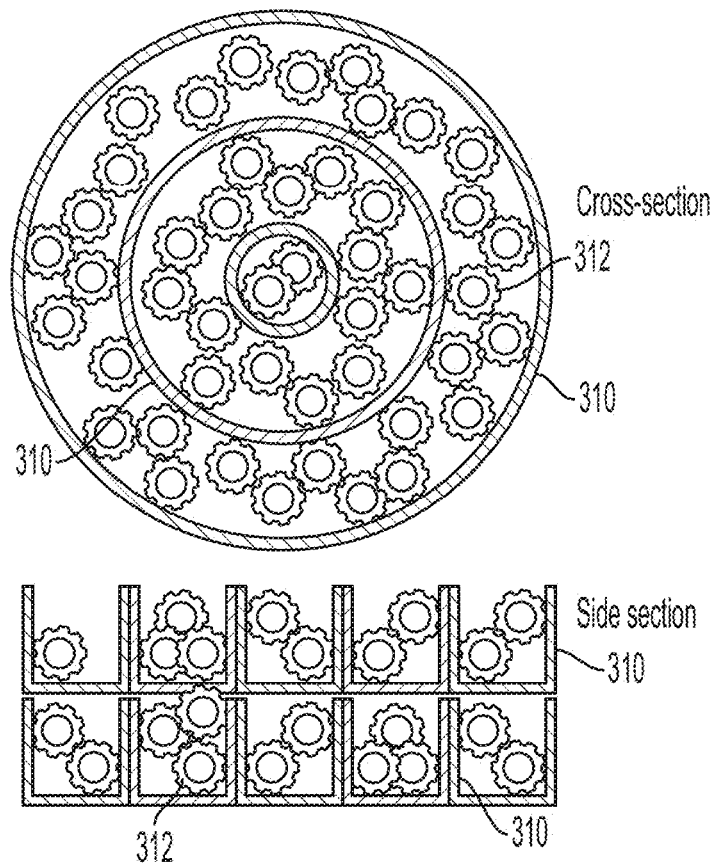

As shown in FIG. 13, adhesives, as described above, can be used to provide lateral confinement 310 of fluid-philic elements 312 such as spores. FIG. 13 illustrates that other types of lateral confinement 310 may be employed such as a pattern of hoop-shaped fences that retain the fluid-philic elements 312. The fences may be patterned on a substrate, for example, by molding, etching, 3D printing or other means, and be provided with lateral-axis openings to facilitate the perfusion of all the fluid-philic elements 312.

Figure 14:
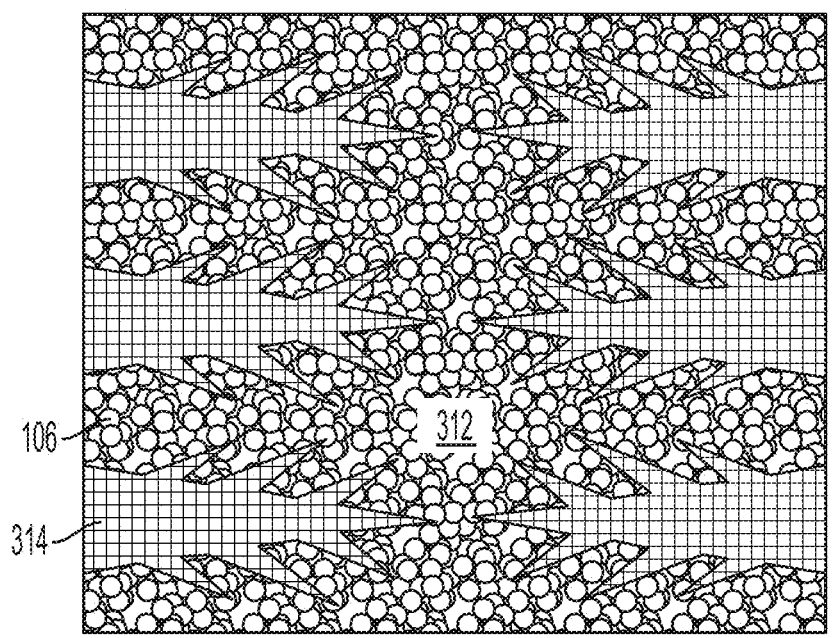

In another aspect, the fluid-responsive material can simultaneously serve as the actuator and the wicking material, because capillary forces in the channels can wick the fluid from a reservoir and distribute to the channel network. More fluid will be drawn from the reservoir as the actuator material absorbs the fluid. Referring to FIG. 14, actuator 106 and wicking material 314 are shown. FIG. 14 shows actuator 106 in which a wicking material 314 is used to promote the wetting of fluid-philic elements 312 in addition to, or instead of, using convective perfusion. In embodiments, wicking material 314 may have a scaffold that helps to resist crushing when the fluid-philic elements 312 expand. Such a scaffold may also provide for lateral retention of fluid-philic elements 312. It will be evident that wicking material 314 is shown with a tree-like structure and as elsewhere disclosed, the purpose of this may be to promote rapid wetting of the fluid-philic elements 312.

In any of the embodiments in which water is used to actuate a hygroscopic material-based actuator, it will be understood that the aspects described herein are not limited to the philicity of water and hygroscopic material but may be extended to other types of fluid-material philicity (e.g., an attraction that induces a capillary-type of force causing a fluid to be drawn into a material and generate a forceful expansion). Any of the aspects may be modified by changing the recitation of water and a hygroscopic material, such as spores or cellophane, to provide new aspects based on other fluid-material combinations that exhibit philicity.

It will be observed that the use, for example, of stiff hygroscopic (or other fluid-philic materials) avoids the requirement of a pressure-vessel to contain the material that absorbs the fluid to create an expansion. Using various devices and methods, a compact actuator is enabled that is not dependent on an external pressure vessel for confining a more isotopically expanding material as in prior art devices using hygroscopic materials.

In one aspect, the actuators described herein can be used to deliver viscous drugs at a higher concentration per injection permitting patients or caregivers to inject doses of medications at home over a shorter period. In contrast, current actuators require long term, intravenous injections in a hospital or other medical facility. In addition, more viscous drugs require the use of larger gauge needles causing unnecessary pain. Delivery of viscous drugs using the actuators described herein can utilize a narrower gauge needle.

In one aspect, the fluid activated actuators can be used to inject viscous drug formulations with volumes in the range of 0.1 mL and larger through thin needles (e.g., 27 Gauge needles with half an inch length) under short injection times (preferably less than 15 seconds for pen-type auto injector applications and less than 10 minutes for wearable injectors). Such uses require generation of large forces by the actuator driving the plunger. To generate such large forces and deliver required volumes of the drug, the fluid responsive actuator can be sufficiently large in dimensions. Increasing the effective cross-section area of the fluid responsive actuator enhances the forces generated by the actuator, increases the length (in the direction of plunger movement) and increases the volume that can be injected in a given amount of time. Dimensions of the actuator can be determined based on pressure requirements of a particular drug formulation's viscosity, dose, syringe needle dimensions, and the pressure generated by the fluid responsive actuator. The magnitude of pressure required to deliver the drug can be estimated using the Hagen-Poiseuille equation describing viscous flows in pipes in the low Reynolds number regime.

A fluid-responsive actuator to be used in pen type auto-injectors can be designed to have an overall shape of a cylinder with the long axis aligned with the direction of plunger movement. Other prismatic shapes and shapes with varying cross section area and shape can also be used. Because the cross-section area of the fluid responsive material determines the forces being generated upon introduction of the fluid, generating enough forces require this area to be sufficiently large. The cross section (perpendicular to the length of the actuator in the direction of plunger movement) is preferably larger than 9 millimeter-square for applications involving low viscosity drugs (viscosities less than 20 cP) and preferably larger than 100 millimeter-square for applications involving high viscosity drugs (viscosities greater than or equal to 20 cP).

In the case of actuators with non-uniform cross sections along the length of the actuator, the cross-section is defined as the average cross section (volume of the actuator divided by its length along the direction of plunger movement). The channels placed in the actuator should be excluded when determining the volume and the cross-section area. A factor that affects the delivery volume is the plunger cross section area. Plunger diameters of typical syringes are in the range of about 3 mm to about 15 mm. However, the aspects described herein can work with other dimensions of syringes or drug containing vessels with different shapes and without plungers (for example a bag containing a drug wherein the bag is squeezed between the fluid-responsive actuator and another surface placed opposite to the fluid-responsive actuator. Another factor that can affect the delivery volume is the length of the fluid-responsive actuator along the direction of plunger movement and the expansion ratio (strain) of the fluid-responsive actuator upon absorption of the fluid. The length of the fluid-responsive actuator and the expansion ratio determines how large of a distance the plunger can be pushed, which, in turn, determines how large of a volume of drug can be injected. The length of the fluid-responsive actuator is preferably larger than 10 mm Fluid-responsive actuators having lengths larger than about 20 cm and cross section areas more than 2800 $mm^2$ (approximate area of a circle with 6 cm radius) can make it difficult for a patient or a caregiver to handle injectors containing fluid-responsive actuators. Due to space limitations, fluid-responsive actuators with high power-to-volume ratios are advantageous.

In another aspect, the actuators described herein operate at high pressure once activated with water or other activating materials. However, the actuators are low pressure devices until activated and thus can be safely stored and transported. Spring actuators risk accidental mechanical triggering and can lose their stored energy due to inelastic deformation over time.

Although the above description refers to particular aspects, it is to be understood that these aspects are merely illustrative. It will be apparent to those skilled in the art that various modifications and variations can be made to the fluid responsive actuators, fluid responsive elements, fluid responsive injectors, and methods described herein. Thus, it is intended that the present description include modifications and variations that are within the scope of the appended claims and their equivalents.

The invention claimed is:

1. A fluid responsive actuator comprising a plurality of fluid responsive elements, the plurality of fluid responsive elements having a tensile modulus larger than about 100 megapascals (MPa), wherein the plurality of fluid responsive elements are capable of generating a power-to-volume ratio sufficient to inject a drug from a syringe within an injection period from about 1 to about 60 seconds after exposure of the plurality of fluid responsive elements to a fluid, and wherein the power-to-volume ratio is at least about 10 kW $m^{-3}$.

2. The fluid responsive actuator of claim 1, wherein the injection period is about 10 seconds.

3. The fluid responsive actuator of claim 1, wherein the plurality of fluid responsive elements are selected from a group consisting of one or more of spores, cellophane, paper, cellulose, and regenerated cellulose.

4. The fluid responsive actuator of claim 3, wherein the plurality of fluid responsive elements further comprise a confining material to reduce lateral movement of the plurality of fluid responsive elements.

5. The fluid responsive actuator of claim 1, wherein the plurality of fluid responsive elements are spores selected from the group consisting of *Bacillus subtilis, Bacillus thuringiensis* and *Bacillus cereus*.

6. A fluid responsive injector comprising a fluid chamber, a fluid responsive actuator, and a release mechanism for controlling contact between a fluid in the fluid chamber and the fluid response actuator, a drug chamber having a discharge orifice, and a movable fluid-tight barrier positioned between the fluid responsive actuator and the drug chamber, wherein after the release mechanism permits contact between the fluid from the fluid chamber and the fluid responsive actuator, the fluid responsive actuator expands and exerts sufficient force on the movable fluid-tight barrier to push a drug in the drug chamber through a needle that has been affixed to the discharge orifice within an injection period from about 1 to about 60 seconds after exposure of the fluid responsive actuator to flail the fluid, wherein the fluid responsive actuator comprises a plurality of fluid responsive elements that collectively have a cross section perpendicular to a length of the fluid responsive actuator in a direction of movement of the plurality of fluid responsive elements, and wherein the cross section has an area that is either (a) between about 9 $mm^2$ to about 200 $mm^2$ for a drug with a viscosity of less than 20 cP or (b) between about 100 $mm^2$ to about 1000 $mm^2$ for a drug with a viscosity of greater than or equal to 20 cP.

7. The fluid responsive injector of claim 6, wherein the cross section has an area that is between about 9 $mm^2$ to about 200 $mm^2$ and the drug has a viscosity of less than 20 cP.

8. The fluid responsive injector of claim 6, wherein the cross section has an area that is between about 100 $mm^2$ to about 1000 $mm^2$ and the drug has a viscosity of greater than or equal to 20 cP.

9. The fluid responsive injector of claim 6, wherein the plurality of fluid responsive elements are arranged in a plurality of layers, and the plurality of layers are stacked to form a layered architecture.

10. The fluid responsive injector of claim 9, wherein the plurality of layers are attached to each other with an adhesive.

* * * * *